United States Patent [19]

Rodgers et al.

[11] Patent Number: 5,532,357

[45] Date of Patent: Jul. 2, 1996

[54] METHOD FOR PREPARING N-MONOSUBSTITUTED AND N,N'-DISUBSTITUTED UNSYMMETRICAL CYCLIC UREAS

[75] Inventors: James D. Rodgers, Landenberg, Pa.; Jung-Hui Sun, Hockessin, Del.

[73] Assignee: The DuPont Merck Pharmaceutical Company, Wilmington, Del.

[21] Appl. No.: 481,683

[22] Filed: Jun. 7, 1995

[51] Int. Cl.⁶ ............................. C07D 243/08; A61K 31/55
[52] U.S. Cl. ............................................ 540/492; 514/218
[58] Field of Search ............................................ 540/492

[56] References Cited

FOREIGN PATENT DOCUMENTS

| | | | |
|---|---|---|---|
| WO93/07128 | 4/1993 | WIPO | 540/492 |
| WO94/19329 | 9/1994 | WIPO | 540/492 |

OTHER PUBLICATIONS

M. A. Eissenstat and J. D. Weaver, J. Org. Chem. (1993), 58, 3387–3390 A Retro–Diels–Alder Approach to Oxazoles and Imidazoles.

H. Kohn et al, J. Org. Chem. (1977), 42(6), 941–948 Syntheses and Spectral Properties of Substituted Imidazolidinones and Imidazolines.

Primary Examiner—Robert T. Bond

[57] ABSTRACT

The present invention relates generally to methods for the preparation of unsymmetrically substituted cyclic ureas of the formulae

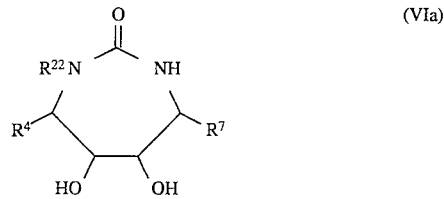

(VIa)

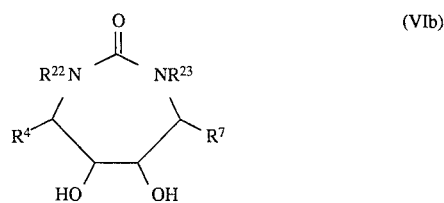

(VIb)

which are useful as HIV protease inhibitors. The methods provided go through an isourea intermediate.

11 Claims, No Drawings

METHOD FOR PREPARING N-MONOSUBSTITUTED AND N,N'-DISUBSTITUTED UNSYMMETRICAL CYCLIC UREAS

FIELD OF THE INVENTION

The present invention relates generally to methods for the preparation of unsymmetrically substituted cyclic ureas useful as HIV protease inhibitors.

BACKGROUND OF THE INVENTION

M. A. Eissenstat and J. D. Weaver (J. Org. Chem. 58(12), 3387–3390, (1993)) disclose the direct formation of a cyclic isourea from a diamine by reactiing cis-exo- 2,3-diamino-5-norbornene and tetraethylorthocarbonate in the presence of acetic acid. (Scheme 1)

Scheme 1

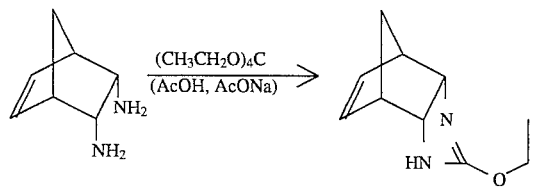

H. Kohn et. al. (J. Org. Chem. 42, 941, (1977)) disclose the formation of a cyclic isourea from a cyclic urea by reacting a N-acetyl cyclic urea and triethyloxonium tetrafluoroborate. (Scheme 2)

Scheme 2

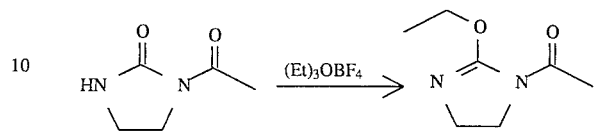

Copending commonly assigned U.S. patent application Ser. No. 08/230,562, filed Apr. 20, 1994, claims a process for the preparation of symmetrically or unsymmetrically nitrogen-disubstituted or -monosubstituted cyclic ureas having a broad range of hydroxy protecting groups for the diol as shown in Scheme 3. In that process, chromatographic separation of the unsubstituted and N-monosubstituted cyclic urea is required.

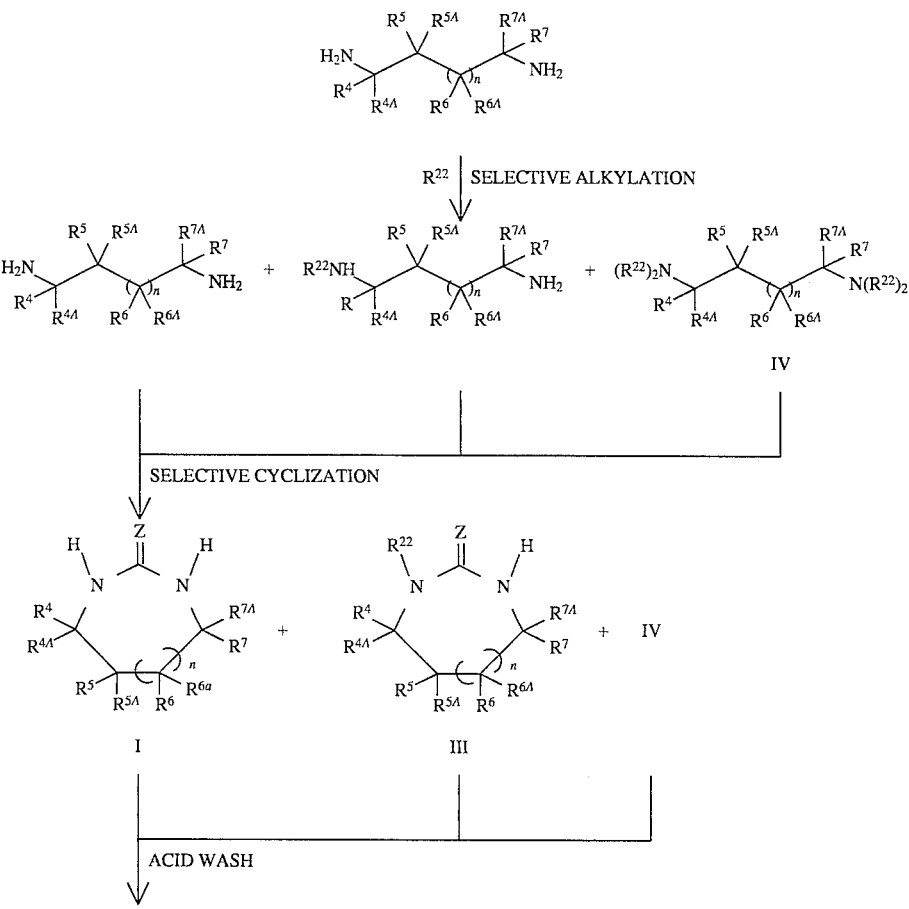

-continued
Scheme 3

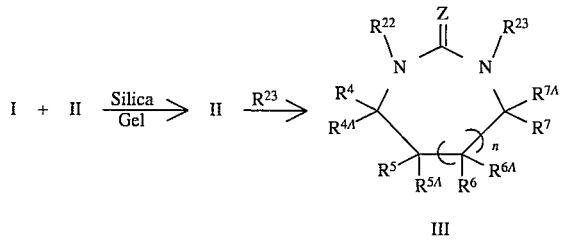

Copending commonly assigned U.S. patent application Ser. No. 08/197,630, filed Feb. 16, 1994, discloses a process for the preparation of symmetrically or unsymmetrically N,N'-disubstituted or N-monosubstituted cyclic ureas, having a broad range of hydroxyl protecting groups, via cyclization of an un- ($R^{22}$ and $R^{23}$ are H), mono- (one of $R^{22}$ and $R^{23}$ are H while the other is nonhydrogen) or disubstituted (both $R^{22}$ and $R^{23}$ are not hydrogen) linear diamine to the respective cyclic urea as shown in Scheme 4. The same application teaches that unsymmetrical N,N'-disubstituted cyclic ureas can be synthesized by reacting an N,N'-unsubstituted cyclic urea with less than two equivalents of an alkylating agent followed by chromatographic separation of the resulting mixture comprising of unsubstituted cyclic urea, N-monosubstituted cyclic urea, and symmetrical N,N'-disubstituted cyclic urea. Alkylation of the N-monosubstituted cyclic urea with an alkylating agent in the presence of strong base then provides unsymmetrical N,N'-disubstituted cyclic ureas.

Scheme 4

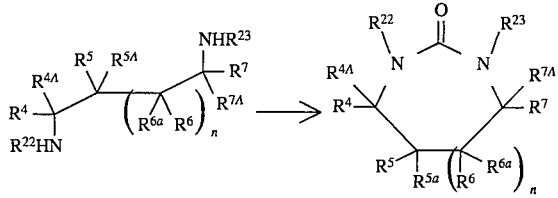

Also disclosed in U.S. Ser. No. 08/197,630 is the cyclization of a nitrogen-unsubstituted acetonide protected diaminodiol with CDI in methylene chloride, albeit in low yields. The yield of this cyclization could be improved by conducting it in refluxing tetrachloroethane. The cyclization of a nitrogen-unsubstituted bis-Mem protected diaminodiol was shown to occur in high yield. The use of acyclic diol protecting groups allowed for high cyclization yields but produced intermediates which were undesirable oils. These intermediates also lead to lower yields in subsequent steps of the process. The cyclization of a bis-Mem protected bis-monophenylhydrazinodiol (I) with phosgene to the corresponding cyclic urea (II) (as shown in Scheme 5) was disclosed in the same reference.

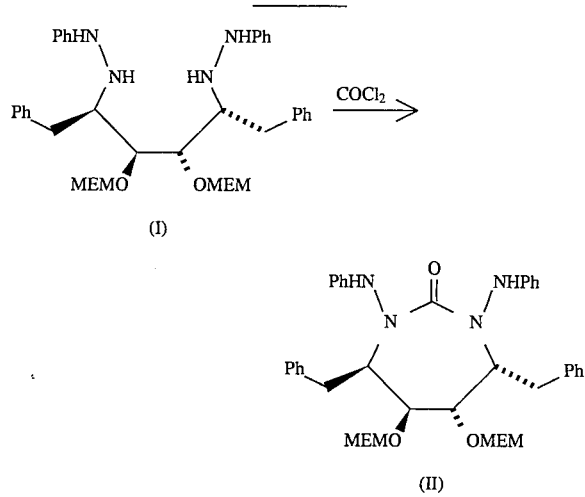

Scheme 5

Although unsymmetrical N,N'-disubstituted cyclic ureas can be made by the methods described above, the products are often contaminated with symmetrical N,N'-disubstituted urea and yields are generally variable and low. Both procedures also give varying amounts of unalkylated cyclic urea.

Since unsymmetrical N,N'-disubstituted cyclic ureas are less crystalline and more soluble, they may prove advantageous in formulations and oral bioavailability over their symmetrical counterparts. In addition, unsymmetrical N,N'-disubstituted cyclic ureas may prove superior from a resistance standpoint; a major concern for HIV protease inhibitors. Clearly, a process which provides these compounds in good yield and purity is of considerable commercial value.

Despite the various methods for their preparation, there still exists a need for more efficient and cost-effective methods for the preparation of such unsymmetrical N,N'-disubstituted and N-monosubstituted cyclic urea HIV protease inhibitor compounds in high yields. The present invention provides improved processes for the synthesis of such compounds and processes for the synthesis of intermediates for their synthesis. This invention provides pure N-monoalkylated or N,N'-unsymmetrical dialkylated material in good yield without contamination by symmetrical byproducts or unalkylated urea.

SUMMARY OF THE INVENTION

[1] There is provided by this invention a process for the preparation of compounds of the formulae (VIa) and (VIb):

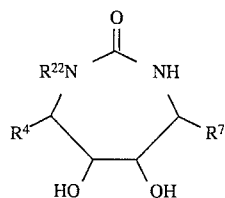
(VIa)

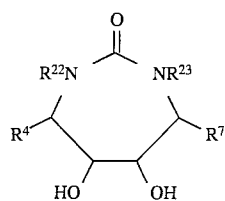
(VIb)

or pharmaceutically acceptable salts or prodrug forms thereof wherein:

$R^4$ and $R^7$ are the same and are selected from the group consisting of:

$C_1$–$C_8$ alkyl substituted with 0–3 $R^{11}$; $C_2$–$C_8$ alkenyl substituted with 0–3 $R^{11}$; and $C_2$–$C_8$ alkynyl substituted with 0–3 $R^{11}$;

$R^{11}$ is independently selected at each occurrence from the group consisting of;

H, keto, halogen, cyano, —$CH_2NR^{13}R^{14}$, —$NR^{13}R^{14}$, —$CO_2R^{13}$, —$OC(=O)R^{13}$, —$OR^{13}$, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)(OR^{13})_2$, $C_1$–$C_4$ alkyl, $C_2$–$C_4$ alkenyl, $C_3$–$C_6$ cycloalkylmethyl, phenyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino)ethoxy, azido, —$C(R^{14})=N(OR^{14})$;

$C_3$–$C_{10}$ cycloalkyl substituted with 0–2 $R^{12}$;

$C_1$–$C_4$ alkyl substitued with 0–2 $R^{12}$;

aryl($C_1$–$C_3$ alkyl)-, substituted with 0–2 $R^{12}$;

$C_2$–$C_6$ alkoxyalkyl-, substituted with 0–2 $R^{12}$;

$C_1$–$C_4$ alkylcarbonyloxy substituted with 0–2 $R^{12}$;

$C_6$–$C_{10}$ arylcarbonyloxy substituted with 0–2 $R^{12}$;

a $C_5$–$C_{14}$ carbocyclic residue substituted with 0–3 $R^{12}$; and a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is independently selected at each occurrence from the group consisting of;

H, keto, halogen, cyano, —$CH_2N(R^{13A})R(^{14A})$, —$OR^{13A}$ —$N(R^{13A})R(^{14A})$, —$CO_2H$, —$OC(=O)$ ($C_1$–$C_3$ alkyl), —OH, $C_2$–$C_6$ alkoxyalkyl, —$C(=O)NH_2$, —$OC(=O)NH_2$, $NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl($C_1$–$C_3$ alkyl);

$C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;

a 5- to 10-membered heterocyclic ring system containing 1 to 4 heteroatoms independently selected from oxygen, nitrogen or sulfur, said heterocyclic ring system substituted with 0–3 $R^{12A}$;

—$SO_mR^{13A}$, $C_1$–$C_4$ haloalkyl, $C_1$–$C_4$ haloalkoxy, $C_1$–$C_4$ alkoxy, $C_2$–$C_4$ alkynyl, phenyl, said phenyl being optionally substituted with Cl, F, Br, CN, $NO_2$, $CF_3$, $C_1$–$C_4$ alkyl, $C_1$–$C_4$ alkoxy or OH; and $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy, $NH_2$ or OH;

$R^{12}$, when a substituent on carbon, is independently selected at each occurrence from the group consisting of;

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, —$NR^{13}R^{14}$, $C_1$–$C_4$ alkyl substituted with —$NR^{13}R^{14}$, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$;

a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; and when $R^{12}$ is attached to a saturated carbon atom, it may be =O or =S; or when $R^{12}$ is attached to sulfur it may be =O.

$R^{12}$, when a substituent on nitrogen, is independently selected at each occurrence from the group consisting of;

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, and —$C(R^{14})=N(OR^{14})$;

$R^{12A}$, when a substituent on carbon, is independently selected at each occurrence from the group consisting of;

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13A}$, $C_1$–$C_4$ alkyl substituted with —$NH_2$, —$NH_2$, —NHMe, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mMe$, —$SO_2NH_2$, —$NHSO_2Me$, —$OCH_2CO_2R^{13A}$, 2-(1-morpholino) ethoxy;

a 5- or 6-membered heterocyclic ring containing from 1 to 4 heteroatoms independently selected from oxygen, nitrogen or sulfur;

$R^{12A}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NH_2$; and when $R^{12A}$ is attached to a saturated carbon atom, it may be =O or =S; or when $R^{12A}$ is attached to sulfur it may be =O.

$R^{12A}$, when a substituent on nitrogen, is independently selected at each occurrence from the group consisting of;

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, and $C_1$–$C_4$ alkylcarbonyl;

$R^{13}$ is independently selected at each occurrence from the group consisting of;

H; heterocycle substituted with 0–3 $R^{11A}$ and 0–1 $R^{16}$; phenyl substituted with 0–3 $R^{11A}$; benzyl substituted with 0–3 $R^{11A}$; $C_1$–$C_6$ alkyl substituted with 0–3 $R^{11A}$; $C_2$–$C_4$ alkenyl substituted with 0–3 $R^{11A}$; $C_1$–$C_6$ alkylcarbonyl substituted with 0–3 $R^{11A}$; $C_1$–$C_6$ alkoxycarbonyl substituted with 0–3 $R^{11A}$; $C_1$–$C_6$ alkylaminocarbonyl substituted with 0–3 $R^{11A}$; $C_3$–$C_6$ alkoxyalkyl substituted with 0–3 $R^{11A}$; an amine protecting group when $R^{13}$ is bonded to N; and a hydroxyl protecting group when $R^3$ is bonded to O;

$R^{14}$ is independently selected at each occurrence from the group consisting of;

hydrogen, $C_1$–$C_6$ alkoxy, $C_2$–$C_6$ alkenyl, phenyl, benzyl, an amine protecting group when $R^{14}$ is bonded to N, a hydroxyl or carboxyl protecting group when $R^{14}$ is bonded to O; and $C_1$–$C_6$ alkyl substituted with 0–3 groups selected from OH, $C_1$–$C_4$ alkoxy, halogen, $R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group consisting of:

H and $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, —CN, —$NO_2$, $C_1$–$C_4$ haloalkyl, $C_1$–$C_4$ haloalkoxy, $C_1$–$C_4$ alkoxy, $C_1$–$C_6$ alkyl, $C_2$–$C_4$ alkenyl, $C_2$–$C_4$ alkynyl, phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, CN, $NO_2$, $CF_3$, $C_1$–$C_4$ alkyl, $C_1$–$C_4$ alkoxy or OH; or $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

m is 0, 1 or 2;

$R^{22}$ and $R^{23}$ are independently selected at each occurrence from the group consisting of;

$C_1$–$C_8$ alkyl substituted with 0–3 $R^{31}$; $C_2$–$C_8$ alkenyl substituted with 0–3 $R^{31}$; $C_2$–$C_8$ alkynyl substituted with 0–3 $R^{31}$; $C_3$–$C_{14}$ carbocyclic ring system substituted with 0–5 $R^{31}$ and 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is independently selected at each occurrence from the group consisting of;

—OH, $C_1$–$C_4$ alkoxy, —$CO_2R^{15}$, —$COR^{15}$, keto, halogen, cyano, —$CH_2NR^{13}R^{14}$, —$NR^{13}R^{14}$, —$CO_2R^{13}$, —C(=O)$R^{11}$, —OC(=O)$R^{13}$, —$OR^{13}$, $C_2$–$C_6$ alkoxyalkyl, —$S(O)_mR^{13}$, —NHC(=NH)NHR$^{13}$, —C(=NH)NHR$^{13}$, —C(=O)NR$^{13}R^{14}$, —NR$^{14}$C(=O)R$^{13}$, =NOR$^{14}$, —NR$^{14}$C(=O)OR$^{14}$, —OC(=O)NR$^{13}R^{14}$, —NR$^{13}$C(=O)NR$^{13}R^{14}$, —NR$^{13}$C(=S)NR$^{13}R^{14}$, —NR$^{14}$SO$_2$NR$^{13}R^{14}$, —NR$^{14}$SO$_2R^{13}$, —SO$_2$NR$^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —NR$^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2R^{13}$, 2-(1-morpholino)ethoxy, azido, —C(R$^{14}$)=N(OR$^{14}$);

a $C_5$–$C_{14}$ carbocyclic residue substituted with 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is independently selected at each occurrence from the group consisting of;

phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2R^{14}$, benzyloxy, halogen, 2-(1-morpholino)ethoxy, —CO$_2R^{13}$, hydroxamic acid, —CONR$^{13}$NR$^{13}R^{14}$, cyano, sulfonamide, —CHO, $C_3$–$C_6$ cycloalkoxy, —NR$^{13}R^{14}$, —C(R$^{14}$)=N(OR$^{14}$), —NO$_2$, —OR$^{13}$, —NR$^{40}R^{41}$, —SO$_mR^{13}$, —SO$_m$NR$^{13}R^{14}$, —C(=O)NR$^{13}R^{14}$, —OC(=O)NR$^{13}R^{14}$, —C(=O)R$^{11}$, —OC(=O)R$^{11}$, —B(OH)$_2$, —OCO$_2R^{13}$, phenyl, —C(=O)NR$^{13}$—(C$_1$–C$_4$ alkyl)—NR$^{13}R^{14}$, —C(=O)NR$^{40}R^{41}$, $C_1$–$C_4$ haloalkyl, $C_1$–$C_4$ haloalkoxy, $C_2$–$C_4$ haloalkenyl, $C_1$–$C_4$ haloalkynyl;

—C(=O)NR$^{13}$C(R$^{11}$)$_2$NR$^{13}R^{14}$,
—C(=O)NR$^{13}$C(R$^{11}$)$_2$NR$^{13}$CO$_2R^{13}$,
—C(=O)NR$^{13}$—(C$_1$–C$_4$ alkyl)—NR$^{13}$CO$_2R^{13}$,
—C(=O)N(R$^{13}$)—(C$_1$–C$_4$ alkyl)—R$^{11}$,
—C(=O)C(R$^{11}$)$_2$NR$^{13}R^{14}$, —C(=O)C(R$^{11}$)$_2$NR$^{13}$CO$_2$R$^{13}$, —C(=O)—(C$_1$–C$_4$ alkyl)—NR$^{13}$R$^{14}$, —C(=O)—(C$_1$–C$_4$ alkyl)—NR$^{13}$CO$_2$R$^{13}$;

—(CH$_2$)$_p$OR$^{13}$, —(CH$_2$)$_p$NHR$^{13}$, —(CH$_2$)$_p$CONHR$^{13}$, —(CH$_2$)$_p$SO$_2$NHR$^{13}$, —(CH$_2$)$_n$NHCOR$^{13}$, —(CH$_2$)$_p$NHCO$_2$R$^{13}$, —(CH$_2$)$_n$OCONHR$^{13}$, —(CH$_2$)$_p$NHCONHR$^{13}$, —(CH$_2$)$_p$C(=NH)NHR$^{13}$;

C$_1$–C$_4$ alkoxy substituted with 0–4 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH;

C$_1$–C$_4$ alkyl substituted with 0–4 groups selected from: R$^{11}$, =NR$^{14}$, =NNR$^{13}$C(=O)NR$^{13}$R$^{14}$, =NNR$^{13}$C(=O)OR$^{13}$, or —NR$^{13}$R$^{14}$;

C$_2$–C$_4$ alkenyl substituted with 0–4 R$^{11}$, C$_2$–C$_4$ alkynyl substituted with 0–4 R$^{11}$;

a 5- or 6-membered heterocyclic ring containing from 1 to 4 heteroatoms independently selected from oxygen, nitrogen or sulfur, substituted with 0–2 R$^{12}$;

R$^{32}$ may be a 3- or 4- carbon chain attached to adjacent carbons on the ring to form a fused 5- or 6-membered ring, said 5- or 6- membered ring being optionally substituted on the aliphatic carbons with halogen, C$_1$–C$_4$ alkyl, C$_1$–C$_4$ alkoxy, hydroxy, or —NR$^{13}$R$^{14}$;

when R$^{32}$ is attached to a saturated carbon, it may be =O, =S, =NOH; and when R$^{32}$ is attached to sulfur it may be =O;

p is 0, 1, or 2 n is 1 or 2;

R$^{32}$, when a substituent on nitrogen, is independently selected at each occurrence from the group consisting of:

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, C$_1$–C$_4$ alkylcarbonyloxy, C$_1$–C$_4$ alkylcarbonyl, and —C(R$^{14}$)=N(OR$^{14}$);

R$^{40}$ is selected from: H or C$_1$–C$_3$ alkyl; and

R$^{41}$ is selected from:

—C(=O)NR$^{13}$R$^{14}$; —C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$; —C(=O)H;
—C(=O)R$^{11}$; —C(=O)—(C$_1$–C$_4$ alkyl)—NR$^{13}$R$^{14}$;
—C(=O)—(C$_1$–C$_4$ alkyl)—NR$^{13}$CO$_2$R$^{13}$; or 1–3 amino acids linked together via amide bonds, and linked to the N atom via the carboxylate terminus; and all functional groups, such as amines, carboxyls, ketones, aldehydes, hydrazines, guanidines, hydroxamic acids, alcohols, oximes, and thiols, that are reactive with the chemistry of this process are protected in such a form that the protecting groups may be kept or removed;

said process comprising the steps of: step (1a): direct isourea formation: contacting a compound of the formula (X)

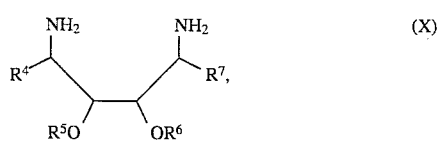

wherein

R$^5$ and R$^6$ are the same and are selected from the group consisting of:

C$_1$–C$_6$ alkyl substituted with 0–3 R$^{11}$; C$_3$–C$_6$ alkoxyalkyl substituted with 0–3 R$^{11}$; C$_1$–C$_6$ alkylcarbonyl substituted with 0–3 R$^{11}$; C$_1$–C$_6$ alkoxycarbonyl substituted with 0–3 R$^{11}$; C$_1$–C$_6$ alkylaminocarbonyl substituted with 0–3 R$^{11}$; benzoyl substituted with 0–3 R$^{12}$; phenoxycarbonyl substituted with 0–3 R$^{12}$; phenylaminocarbonyl substituted with 0–3 R$^{12}$; a hydroxyl protecting; or any group that, when administered to a mammalian subject, cleaves to form a free hydroxyl group; or R$^5$ and R$^6$ may alternatively be taken together, along with the oxygen atoms to which they are attached, to form a group selected from the group consisting of:

O—C(—CH$_2$CH$_2$CH$_2$CH$_2$CH$_2$—)—O—,
—O—C(CH$_2$CH$_3$)$_2$—O—, —O—C(CH$_3$)(CH$_2$CH$_3$)—O—,
—O—C(CH$_2$CH$_2$CH$_2$CH$_3$)$_2$—O—, —O—C(CH$_3$)(CH$_2$CH(CH$_3$)CH$_3$)—O—, —O—CH(phenyl)—O—, —OCH$_2$SCH$_2$O—, —OCH$_2$OCH$_2$O—, —OS(=O)O—, —OC(=O)O—, —OCH$_2$O—, —OC(=S)O—, —OS(=O)$_2$O—, —OC(=O)C(=O)O—, —OC(CH$_3$)$_2$O—, and —OC(OCH$_3$)(CH$_2$CH$_2$CH$_3$)O—;

and where all other substituents are as defined above;

in a solvent with an excess of a tetralkylorthocarbonate, (R$^1$—O)$_4$C, wherein R$^1$ is methyl or ethyl, in the presence of an acid at a suitable temperature for a period of time sufficient to form a compound of the formula (II)

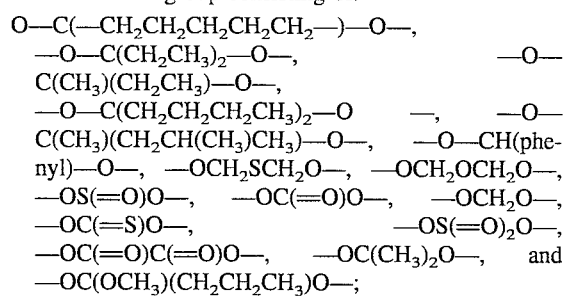

which is optionally isolated; or alternatively, step (1b): urea then isourea formation: contacting, at an appropriate rate, a compound of the formula (X), optionally in the presence of a hindered amine base, in an aprotic solvent with at least 1 molar equivalent of a cyclizing agent at a temperature of ambient to solvent reflux for a period of time sufficient to form a compound of the formula (I)

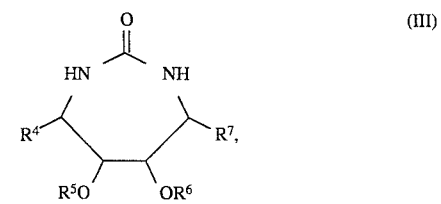

wherein all substituents are as defined above, which is optionally isolated; and contacting a compound of the formula (I) in an aprotic solvent with 1–2 molar equivalents of an oxygen alkylating agent (R$^1$-Y), wherein R$^1$ is as defined above and Y is —OSO$_2$CF$_3$, —OSO$_2$-aryl, —(CH$_3$CH$_2$)$_2$OBF$_4$, or —(CH$_3$)$_2$OBF$_4$, for a period of time sufficient to form a compound of the formula (II) which is optionally isolated; and step (2): isourea alkylation: contacting a compound of the formula (II) in an aprotic solvent with at least one molar equivalent of a strong base and at least one molar equivalent of a nitrogen alkylating agent R$^{22}$-Z (where R$^{22}$ is as defined for compounds of the formula (VIa) and (VIb) and Z is leaving group such as halide or sulfonate) for a period of time sufficient to form a compound of the formula (III)

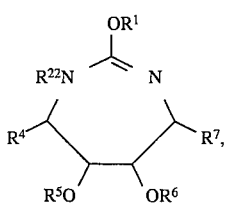

wherein $R^{22}$ is as defined above, which is optionally isolated; and step (3a): monoalkylated isourea alkylation: contacting a compound of the formula (III) in an aprotic solvent with at least one molar equivalent of a nitrogen alkylating agent $R^{23}$-Z for a period of time sufficient to form a compound of the formula (IV)

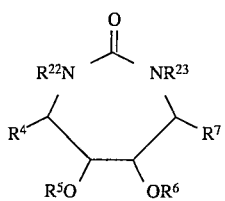

which is optionally isolated; or alternatively after step (2)

step (3b): monoalkylated isourea deprotection and conversion to urea: contacting a compound of the formula (III) with a reagent or condition or combination of reagents and/or conditions for a period of time sufficient to effect the removal of $R^5$, $R^6$ and $R^1$ and to form a compound of the formula (VIa)

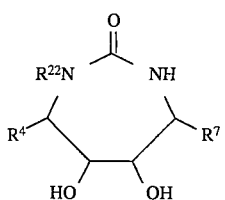

which is isolated; or alternatively after step (2)

step (3c): monoalkylated isourea to monoalkylated urea conversion: contacting a compound of the formula (III) in a solvent with at least 2 molar equivalents of an isourea oxygen dealkylating agent for a period of time sufficient to form a compound of the formula (V)

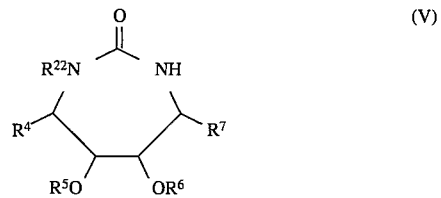

which is optionally isolated; and after step (3c)

step (4c): monoalkylated urea alkylation: contacting a compound of the formula (V) in an aprotic solvent with at least one molar equivalent of a strong base and at least one molar equivalent of a nitrogen alkylating agent $R^{23}$-Z for a period of time sufficient to form a compound of the formula (IV) which is optionally isolated; or alternatively after step (3c)

step (4d): monoalkylated urea deprotection: contacting a compound of the formula (V) with a reagent or condition or combination of reagents and or conditions for a period of time sufficient to effect the removal of $R^5$ and $R^6$ and to form a compound of the formula (VIa) which is isolated; and after steps (3a) and (4c)

step (5): bisalkylated urea deprotection: contacting a compound of the formula (IV) with a reagent or condition or combination of reagents and/or conditions for a period of time sufficient to effect the removal of $R^5$, $R^6$ and any protecting groups and/or to convert functional groups to their desired form to form a compound of the formula (VIb) which is isolated.

The scope of the present invention may be further understood according to Scheme 6.

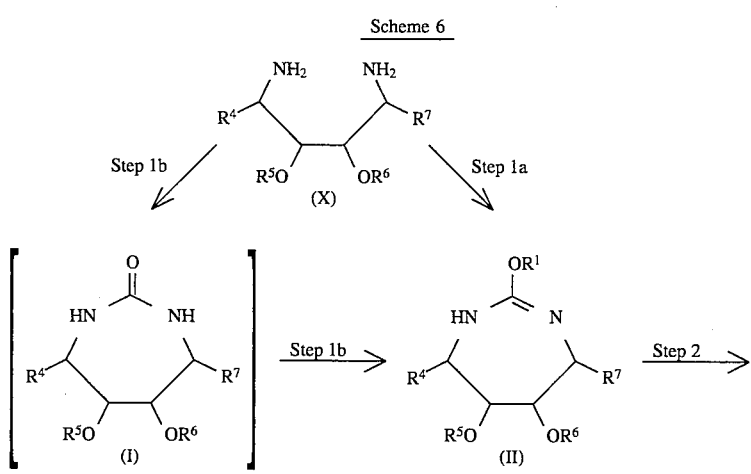

-continued
Scheme 6

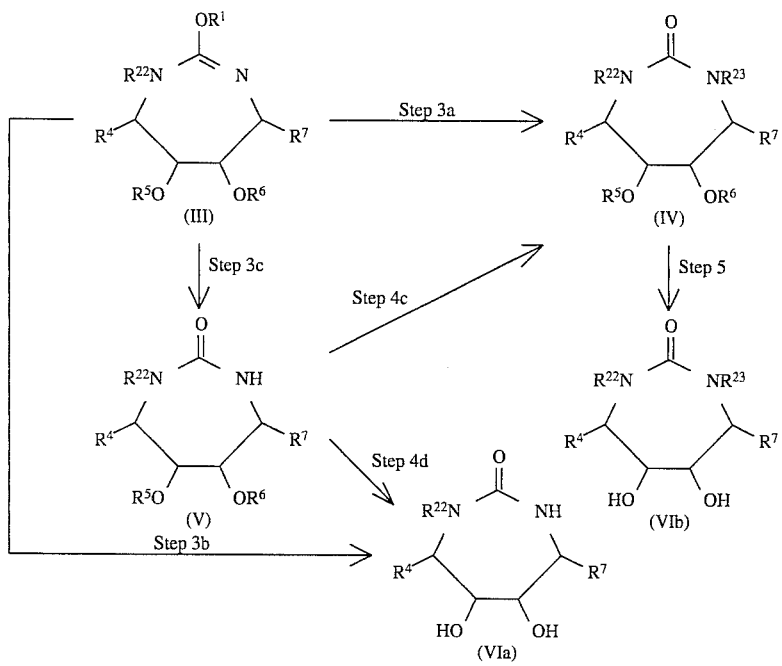

DETAILED DESCRIPTION OF THE INVENTION

The present invention concerns the preparation of N-monoalkylated (formula (VIa)) and unsymmetrical N,N'-dialkylated (formula (VIb)) cyclic ureas from linear diamino diols (formula (X)). In the first step of the invention, a linear diamine (formula (X)) is cyclized either directly or indirectly to an isourea (formula (II)). The direct preparation of compound (II) is accomplished by treating compound (X) with a tetraalkyl orthocarbonate (step (1a)). The indirect preparation of compounds (II) is accomplished by treating compound (X) with a cyclizing agent to form a cyclic urea (I) which is then treated with an oxygen alkylating agent to form the desired compounds (step (1b)). Treatment of compound (II) with a nitrogen alkylating agent affords compound (III) (step (2)). Compound (III) is converted to compound (VIa) via step (3b) by treatment with a combination of reagents and/or conditions that will effect the removal of $R^5$ and $R^6$ and the O-dealkylation of the isourea. Compound (III) may also be converted to compound (VIa) by first treatment with a reagent to remove $R^1$ to form compound (V) (step 3c) and second treatment of (V) with a combination of reagents and/or conditions to remove $R^5$ and $R^6$ (step 4d). Alternatively, compound (III) can be converted to compound (IV) by treatment with a second nitrogen alkyating agent (step 3a). Another route to compound (IV) is treatment of compound (V) with a nitrogen alkylating agent. Finally, compound (IV) is converted to the desired final unsymmetrical N,N'-disubstituted cyclic urea (VIb) by treating it with a combination of reagents and/or conditions which will remove $R^5$, $R^6$ and any other protecting groups and optionally will convert functional groups to their desired form. The process of the present invention is described further below.

step (1a): direct formation of isourea:

This step involves the cyclization of the linear diamine free base or its salt to a cyclic isourea. Thus, compound (X), or optionally its salt in the presence of at least one molar equivalent of a hindered amine base, in the presence of an acid in a solvent is contacted with at least 1 molar equivalent of a tetraalkyl orthocarbonate at a temperature of 50° C. to solvent reflux for a period of 5–72 hrs to form compound (II) which is optionally isolated.

Suitable acids for this step include, by way of example and without limitation, (±) camphorsulfonic acid and related stereoisomers and p-toluenesulfonic acid. The acid may be present in the range of mole of acid catalyst ranging from 0.05–1.0 molar equivalents.

As used herein, the term "tetraalkyl orthocarbonate" refers to a reagent of the formula $(R^1-O)_4C$, wherein $R^1$ is methyl or ethyl.

It is understood that this direct formation of isourea from a linear diamine involves at least two reaction intermediates

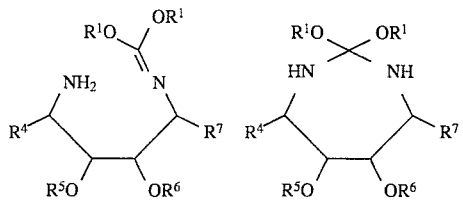

which are not isolated.

The reaction solvent may be the tetraalkylorthocarbonate itself. Other suitable aprotic solvents for this step include, by way of example and without limitation: methylene chloride, toluene, tetrahydrofuran, methyl tert-butyl ether, dimethoxyethane, 1,1,2,2-tetrachloroethane, benzene, cyclohexane, pentane, hexane, cycloheptane, methylcyclohexane, heptane, ethylbenzene, m-, o-, or p-xylene, octane, indane, nonane, naphthalene, 1,3-dioxane, 1,4-dioxane, furan, carbon tetrachloride, hexafluorobenzene, 1,2,4-trichlorobenzene, o-dichlorobenzene, chlorobenzene, or fluorobenzene.

As used herein, the term "hydroxyl protecting group reagent" (or "O-protected") refers to any reagent known in the art of organic synthesis for the protection of hydroxyl groups which may be reacted with an hydroxyl to provide an hydroxyl group protected with an hydroxyl protecting group. Such protecting groups include those listed in Greene and Wuts, "Protective Groups in Organic Synthesis", John Wiley & Sons, New York (1991), the disclosure of which is hereby incorporated by reference. The hydroxyl protecting groups are base-stable and can include, but are not limited to acyl types, aromatic carbamate types, ether types and alkyl types. Exemplary are methyl, methoxymethyl (MOM), methylthiomethyl, benzyloxymethyl, t-butoxymethyl, 2-methoxyethoxymethyl (MEM), 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxyl protecting groups may also include the following protecting groups as ethers: benzyl, allyl, p-methoxybenzyloxymethyl, trichloroethoxymethyl, p-methoxybenzyl, t-butyl, o-nitrobenzyl, triphenylmethyl, oxydimethylene-1,3-diyl, p-methoxyphenyldiphenylmethyl, p-nitrobenzyl, and triisopropylsilyl.

Conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, may include: (a) 1–4 M HCl in anhydrous or aqueous methanol, ethanol, isopropanol, tetrahydrofuran, dioxane, or diethyl ether; (b) 1–4 M $H_2SO_4$ in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Conditions to remove o-nitrobenzyl group include irradiation of the compound at 320 nm wavelength for 5–60 minutes.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with $[Ir(COD)(Ph_2MeP)_2]PF_6$ or $(Ph_3P)_3RhCl$ in tetrahydrofuran, diethyl ether or dioxane followed by hydrolysis with aqueous $HgCl_2$.

The compounds of the present invention may contain a cyclic acetal or ketal hydroxyl protecting group —$OC(CH_3)_2O$— or —$OCH_2OCH_2O$— or other such groups. As used herein, the term "cyclic acetal protecting group" includes any protecting group known in the art of organic synthesis for the protection of 1,2-diol group through formation of a cyclic acetal or cyclic ketal group. Such protecting groups include, but are not limited to, those listed in Greene and Wuts, "Protective Groups in Organic Synthesis", John Wiley & Sons, New York (1991), the disclosure of which is hereby incorporated by reference. Examples of such cyclic acetal or ketal 1,2-diol protecting groups are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, methoxymethylene acetal, and substituted or unsubstituted carbocyclic diethers (such as oxydimethylene-1,3-diyl), dithioethers, mixed ethers, enol ethers or ketones.

step (1b): indirect formation of isourea:

This step comprises the cyclization of the linear diamine free base or salt to a cyclic urea followed by oxygen alkylation to the isourea. Thus, in the first part of this step, compound (X) in an aprotic solvent at −20°–30° C. in an inerted atmosphere, optionally in the presence of 0–2 molar equivalents of a hindered amine base, is contacted with at least one molar equivalent of a suitable cyclizing agent, which may optionally be added at a temperature lower than the reaction temperature, for a period of 10 min to 3 days to form compound (I) which is optionally isolated.

By "cyclizing agent" is meant a reagent or condition or combination of reagents and conditions that can effect the formation of a cyclic urea from the diamine of formula (II). Examples of suitable cyclizing reagents include but are not limited to: phenyl chloroformate, phenyl tetrazoylformate, phosgene, diphosgene, triphosgene, oxalyl chloride, $C_1$–$C_4$ dialkyl carbonate, N,N'-disuccinimidyl carbonate, trichloromethyl chloroformate, 1,1'-carbonyl diimidazole, ethylene carbonate, vinylene carbonate and 2(S),3-pyridinediyl carbonate.

As used herein, a "hindered amine base" is intended to include any of a number of nitrogen containing bases wherein the nitrogen is surrounded by sterically demanding groups such that the nitrogen accessibility is reduced. Examples of hindered amine bases useful for the present invention include, by way of example and without limitation, aromatic and aliphatic amines, alkyl substituted pyridines, 1,8-diazabicyclo[2.2.2]octane (DABCO), pyridine, 4-pyrrolidinopyridine, 4-piperidinopyridine, N,N-dimethylaminopyridine (DMAP), trialkyl amines, triethylamine, N,N-diisopropylethylamine, N,N-diethylcyclohexylamine, N,N-dimethylcyclohexylamine, N,N,N'-triethylenediamine, N,N-dimethyloctylamine, 1,5-diazabicyclo[4.3.0]non-5-ene (DBN), 1,8-diazabicyclo[5.4.0]undec-7-ene (DBU), or tetramethylethylenediamine (TMEDA).

In the second part of this step, compound (I) in an aprotic solvent is contacted with 1–2 molar equivalents of an oxygen alkylating agent ($R^1$-Y) at a temperature of 0°–120° C. for a period of 1–24 hrs to form a compound of the formula (II) which is optionally isolated.

As used herein, the term "oxygen alkylating agent" refers to reagents of the formula $R^1$-Y wherein $R^1$ is methyl or ethyl and Y is a leaving group such as a sulfonate or a dialkyl ether derived from a trialkyloxonium borate. Examples of such reagents include, by way of example and without limitation, methyl triflate, methyl tosylate, methyl benzenesulfonate, trimethyloxonium tetrafluoroborate, and triethyloxonium tetrafluoroborate.

Suitable aprotic solvents for this step include, by way of example and without limitation: methylene chloride, chloroform, toluene, tetrahydrofuran, acetonitrile, methyl tert-butyl ether, dimethoxyethane, ethyl acetate, 1,1,2,2-tetrachloroethane, benzene, cyclohexane, pentane, hexane, cycloheptane, methylcyclohexane, heptane, ethylbenzene, m-, o-, or p-xylene, octane, indane, nonane, naphthalene, tetramethylurea, nitrobenzene, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, carbon tetrachloride, bromodichloromethane, dibromochloromethane, bromoform, chloroform, dibromomethane, butyl chloride, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene.

step (2): isourea alkylation:

This step involves the monoalkylation of the isourea with a nitrogen alkylating agent. Thus, compound (II) in an aprotic solvent is contacted with at least 1 molar equivalent of a strong base and at least 1 molar equivalent of a nitrogen alkylating agent ($R^{22}$-Z) at a temperature of 0°–30° C. for a period of 6–24 hrs to form a compound of the formula (III).

As used herein, the term "nitrogen alkylating agent" refers to a reagent of the formula $R^{22}$-Z or $R^{23}$-Z where $R^{22}$ and $R^{23}$ are as defined above, and Z is a leaving group such as those commonly used in the art of nitrogen alkylation. Suitable Z groups may include halides and sulfonates such as, by way of example and without limitation, Br, Cl, I, and $R^3$—$SO_3$—. Here, $R^3$ is taken to be any group commonly attached to the sulfur atom of sulfonic acids or esters, where said reagents are used as alkylating agents.

As used herein, the term "strong base" refers to a base capable of removing the H from the isourea protonated nitrogen. Suitable bases include, but are not limited to, inorganic bases such as metal alkoxides, phosphates, carbonates and hydrides. Examples of such bases include, by way of example and without limitation, sodium hydride, potassium t-butoxide, potassium hydride, lithium carbonate, sodium carbonate, potassium carbonate, and cesium carbonate.

Suitable aprotic solvents for this step include, by way of example and without limitation, dimethylformamide, dimethylsulfoxide tetrahydrofuran, dimethoxyethane, benzene, toluene, and N-methylpyrrolidone.

step (3a): monoalkylated isourea alkylation:

This step involves alkylation of the second nitrogen of the isourea to form an unsymmetrical N,N'-bisalkylated cyclic urea. In this step, the nitrogen alkylation proceeds concomitantly with the isourea to urea conversion. Thus, compound (III) is treated with a nitrogen alkylating agent ($R^{23}$-Z as described above) at a temperature of 45°–90° C. for a period of 12–24 hrs to form compound (IV) which is optionally isolated.

step (3b): monoalkylated isourea deprotection and conversion to urea:

This step involves the simultaneous deprotection of the diol group and conversion of the isourea to an urea to yield a N-monoalkylated cyclic urea. This step is performed in place of step (3a) when the desired product is a N-monosubstituted rather than N,N'-disubstituted cyclic urea. This step may also be performed alternatively to a combination of steps (3c) and (4d) whose product is the same N-monosubstituted diol protected cyclic urea. Thus, compound (III) is treated with a combination of reagents and/or conditions for a period of time to effect removal of $R^1$, $R^5$, $R^6$, and any other protecting groups to form compound (VIa). An example of such a simultaneous conversion is treatment of compound (III), where $R^1$, $R^5$ and $R^6$ are acid labile groups, with a mineral acid, such as hydrochloric acid or sulfuric acid in in water, or an organic acid, such as trifluoroacetic acid in a solvent or Dowex 50 cation exchange resin in the ($H^+$) form in water, to form compound (VIa). Other suitable solvents include methanol, ethanol, and tetrahydrofuran.

step (3c): monoalkylated isourea to monoalkylated urea conversion:

This step involves the selective conversion of the isourea to an urea while leaving the diol protection groups $R^5$ and $R^6$ intact. The product of this step (V) is carried through to either compound (VIa) via step (4d) or to compound (IV) via step (4c). Thus, compound (III) in a solvent is treated with an isourea oxygen dealkylating agent at a temperature of 30°–250° C. for a period of 0.5–120 hrs to form compound (V) which is optionally isolated.

As used herein, the term "isourea oxygen dealkylating agent" refers to any reagent or combination or reagents and/or conditions which will effect the removal of $R^1$. An example of such a reagent is hydrazine. Thus, when $R^5$ and $R^6$ are a hydrazine stable group such as acetonide or oxydimethylene-1,3-diyl and $R^1$ is methyl, then treatment of compound (III) with hydrazine yields compound (V). When $R^5$ and $R^6$ are a base stable group, sodium hydroxide (1 N) or sodium methoxide in alcohol or water or other suitable solvent may be used to remove $R^1$.

step 4(c): monoalkylated urea alkylation:

This step involves alkylation of the unsubstituted nitrogen of a N-monosubstituted cyclic urea to form an unsymmetrical N,N'-disubstituted cyclic urea. This step is the second of a combination of steps (combined with step (3c)) which provide an alternate pathway for preparing compound (IV). Thus, compound (V) in an aprotic solvent is contacted with at least one molar equivalent of a strong base and at least one molar equivalent of a nitrogen alkylating agent, $R^{23}$-Z, at a temperature of 0°–30° C. for a period of 0.5–24 hrs to form compound (IV).

The preferred strong base is a sodium hydride or potassium t-butoxide.

Suitable aprotic solvents for this step include, by way of example and without limitation, dimethylformamide, dimethylsulfoxide tetrahydrofuran, dimethoxyethane, benzene, toluene, and N-methylpyrrolidone.

step (4d): monoalkylated urea deprotection:

This step involves the removal of the protecting groups from the protected N-monosubstituted cyclic urea to form the deprotected N-monosubstituted cyclic urea. Thus, compound (V) in a solvent is contacted with a combination of reagents and/or conditions for a period of time sufficient to form compound (VIa). An example of such a combination is warm aqueous hydrochloric acid for the removal of $R^5$ and $R^6$ when they are an acid labile group.

A suitable solvent for this step will be chosen according to the particular conversion which is being performed. Such a suitable solvent will be inert to the reaction conditions and reagents; although, it may participate in the deprotection itself.

step (5): N,N'-disubstituted cyclic urea deprotection:

This step involves the deprotection of compound (IV) to form compound (VIb). This step may comprise the removal of more than one protecting group and/or the conversion of functional groups on $R^4$, $R^7$, $R^{22}$ and $R^{23}$ to their desired form. One example of this step is contacting compound (IV), wherein $R^5$ and $R^6$ are taken together to form —OC(CH₃)₂O—, in a solvent with an aqueous mineral acid, such as hydrochloric acid for a period of time sufficient to form compound (VIb).

The judicious selection of solvents for this step is made according to the particular conversion which is being performed.

As described above, the method of the invention may be further understood according to scheme 7. This scheme in no way should be construed as limiting the scope of the invention but serves only to exemplify one of the many embodiments of the present invention.

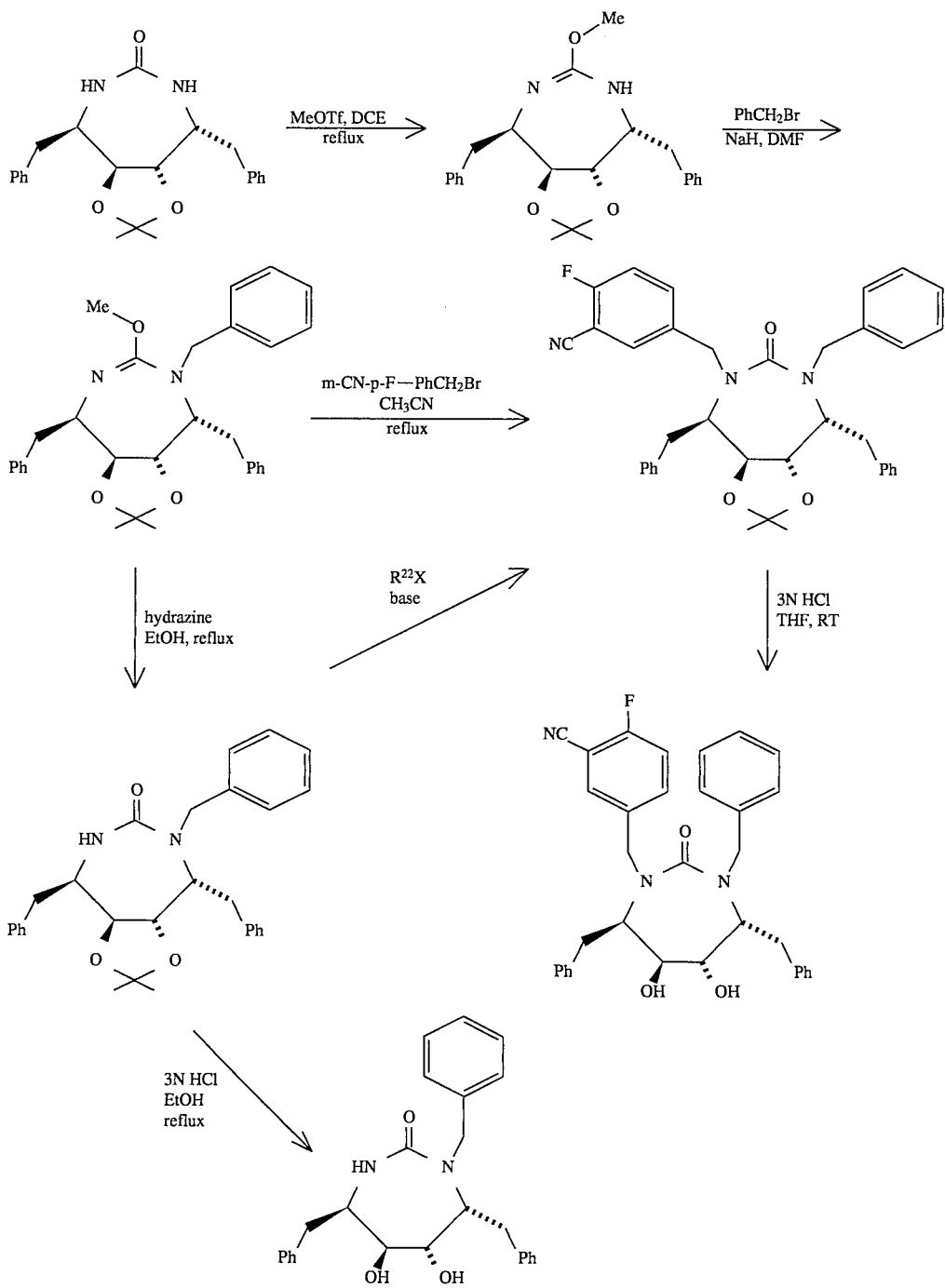

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10 -dioxo-10,10,10, 10-tetrahydrothioxanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

When any variable (for example, $R^{11}$, $R^{12}$, $R^{13}$, $R^{14}$, m, etc.) occurs more than one time in any constituent or formula for a compound, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —C($R^{11}$)$_2$—, each of the two $R^{11}$ substituents on C is independently selected from the defined list of possible $R^{11}$.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, 4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure. Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4αH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, -aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preferred Conditions step (1a):

The preferred hydroxyl protecting group is one in which $R^5$ and $R^6$ are not taken together.

The preferred tetraalkylorthocarbonate is tetraethylorthocarbonate.

step (1b):

The preferred hydroxyl protecting group is acetonide or oxydimethylene-1,3-diyl. When it is acetonide, the preferred conditions for removal are treatment of a compound with such a group in toluene or chlorobenzene with 2–10 molar equivalents of a suitable acid in the presence of 2–50 molar equivalents of an alcohol for a period of 1–4 hr to form a deprotected compound which is isolated.

A preferred cyclizing agent when $R^5$ and $R^6$ are taken together to form —OC(CH$_3$)$_2$O— is phosgene or triphosgene. The preferred molar equivalents of cyclizing agent is 1.0–2.5 for phosgene and 0.4–0.6 for triphosgene.

A preferred cyclizing agent when $R^5$ and $R^6$ are not taken together is carbonyl diimidazole (CDI). It is preferred that 1.1 equivalents of CDI be added.

The preferred reaction solvents include toluene, acetonitrile, tetrahydrofuran, methyl tert-butyl ether, dimethoxyethane, ethyl acetate, 1,1,2,2-tetrachloroethane, and methylene chloride. The more preferred solvent is acetonitrile.

If the salt form of the diamine is used in the reaction, it is preferred that a hindered base be added to the reaction.

The preferred hindered amine base for the reaction with CDI is triethylamine. It is preferred that 1.1 molar equivalents of the hindered amine base be added.

The preferred hindered amine base for the reaction with phosgene is diisopropylethylamine. The preferred molar equivalents of hindered amine base is 2.0–4.0.

The preferred reaction temperature is 0° C. It is preferred that the cyclizing agent be added at a temperature below 0° C. followed by warming of the reaction to 20°–25° C.

The preferred oxygen alkylating agent is methyl triflate.

It is preferred that the cyclizing agent be added in portionwise over the length of the reaction.

step (2):

The preferred strong base is a metal hydride. The preferred metal hydride is sodium hydride.

Scope for product of process:

Preferred in this invention is a process for the preparation of compounds of the formulae (VIa) and (VIb) wherein:

$R^4$ and $R^7$ are independently selected at each occurrence from the group consisting of:

$C_1$–$C_8$ alkyl substituted with 0–3 $R^{11}$; and $C_2$–$C_8$ alkenyl substituted with 0–3 $R^{11}$;

$R^{11}$ is independently selected at each occurrence from the group consisting of:

H, keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, —S(O)$_m$R$^{13}$, $C_2$–$C_4$ alkenyl, $C_3$–$C_6$ cycloalkylmethyl, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl), substituted with 0–2 $R^{12}$, a $C_5$–$C_{14}$ carbocyclic residue substituted with 0–3 $R^{12}$; and a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is independently selected at each occurrence from the group consisting of:

H, keto, halogen, cyano, —CH$_2$N(R$^{13A}$)R($^{14A}$), —OR$^{13A}$, —N(R$^{13A}$)R($^{14A}$), $C_2$–$C_4$ alkenyl, $C_3$–$C_6$ cycloalkylmethyl, $C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;

NO$_2$, $C_1$–$C_6$ alkyl, or phenyl, said phenyl being optionally substituted with Cl, F, Br, CN, NO$_2$, CF$_3$, OCH$_3$ or OH; and a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is independently selected at each occurrence from the group consisting of:

phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —OR$^{13}$, $C_2$–$C_6$ alkoxyalkyl optionally substituted with —Si(CH$_3$)$_3$, $C_1$–$C_4$ hydroxyalkyl, methylenedioxy, ethylenedioxy, —S(O)$_m$R$^{13}$, CF$_3$, 2-(1-morpholino)ethoxy, —CO$_2$H, hydroxamic acid, hydrazide, —C(R$^{14}$)=N(OR$^{14}$), sulfonamide; and a 5- or 6-membered heterocyclic ring containing from 1 to 4 heteroatoms independently selected from oxygen, nitrogen or sulfur.

$R^{12}$, when a substituent on nitrogen, is independently selected at each occurrence from the group consisting of:

benzyl and methyl;

$R^{12A}$, when a substituent on carbon, is independently selected at each occurrence from the group consisting of:

phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —OR$^{13A}$, $C_2$–$C_6$ alkoxyalkyl optionally substituted with —Si(CH$_3$)$_3$, —S(O)$_m$Me; and a 5- or 6-membered heterocyclic ring containing from 1 to 4 heteroatoms independently selected from oxygen, nitrogen or sulfur.

$R^{12A}$, when a substituent on nitrogen, is independently selected at each occurrence from the group consisting of:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkoxycarbonyl, $C_1$–$C_4$ alkylcarbonyloxy, $C_1$–$C_4$ alkylcarbonyl, CF$_3$, 2-(1-morpholino)ethoxy, —CO$_2$H, hydroxamic acid, hydrazide, —C(R$^{14A}$)=N(OR$^{14A}$), and sulfonamide;

$R^{13}$ is independently selected at each occurrence from the group consisting of:

a heterocycle selected from the group consisting of:

[structures of heterocycles: thiazole, thiadiazole, imidazole variants, pyrazoles, oxazole, isoxazole, pyridines, pyrimidines, benzimidazole, benzothiazole, benzoxazole, and various aza-fused bicyclic heterocycles]

said heterocycle substituted with 0–3 $R^{114}$ and 0–1 $R^{16}$;

H; $C_1$–$C_6$ alkyl substituted with 0–3 $R^{114}$; $C_3$–$C_6$ alkoxyalkyl substituted with 0–3 $R^{114}$; $C_2$–$C_4$ alkenyl substituted with 0–3 $R^{114}$; benzyl substituted with 0–3 $R^{114}$; an amine protecting group when $R^{13}$ is bonded to N; and a hydroxyl or carboxyl protecting group when $R^{13}$ is bonded to O;

$R^{14}$ is independently selected at each occurrence from the group consisting of:

hydrogen, $CF_3$, $C_1$–$C_6$ alkyl, $C_1$–$C_6$ alkoxy, $C_2$–$C_6$ alkenyl, benzyl, an amine protecting group when $R^{14}$ is bonded to N, and a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group consisting of:

H and $C_{1-C6}$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected at each occurrence from the group consisting of:

halogen, $NO_2$, CN, $C_1$–$C_6$ alkyl, and phenyl, said phenyl being optionally substituted with Cl, F, Br, CN, $NO_2$, $CF_3$, $OCH_3$ or OH;

$R^{22}$ and $R^{23}$ are independently selected at each occurrence from the group consisting of:

$C_1$–$C_8$ alkyl substituted with 0–3 $R^{31}$; $C_2$–$C_8$ alkenyl substituted with 0–3 $R^{31}$; $C_2$–$C_4$ alkynyl substituted with 0–3 $R^{31}$; $C_6$–$C_{10}$ aryl substituted with 0–3 $R^{31}$ and 0–3 $R^{32}$; and a heterocycle selected from the group consisting of thiazole, indazole, thieno[2,3-c]pyrazole and thieno[3,2-c]pyrazole, said heterocycle substituted with 0–2 $R^{31}$;

$R^{31}$ is independently selected at each occurrence from the group consisting of:

—OH, $C_1$–$C_4$ alkoxy, cyano, nitro, $C_1$–$C_4$ haloalkyl, $C_1$–$C_4$ haloalkoxy, —$CO_2R^{15}$, —$COR^{15}$, keto, halogen, —$CH_2NR^{13}R^{14}$, —$NR^{13}R^{14}$, —$OR^{13}$, $C_2$–$C_6$ alkoxyalkyl, $C_1$–$C_4$ alkyl, $C_2$–$C_4$ alkenyl, $C_3$–$C_{10}$ cycloalkyl, —$CO_2R^{13}$, —$S(O)_mR^{13}$;

a $C_5$–$C_{14}$ carbocyclic residue substituted with 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is independently selected at each occurrence from the group consisting of:

phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, —$CONR^{13}NR^{13}R^{14}$, cyano, sulfonamide, —CHO, $C_3$–$C_6$ cycloalkoxy, —$NR^{13}R^{14}$, —$NO_2$, —$OR^{13}$, —$NR^{40}R^{41}$, —$SO_mNR^{13}$, —$SO_mNR^{13}R^{14}$, —C(=O)$NR^{13}R^{14}$, —OC(=O)$NR^{13}R^{14}$, —C(=O)$R^{11}$, —OC(=O)$R^{11}$, —$OCO_2R^{13}$, phenyl, —C(=O)$NR^{13}$-($C_1$–$C_4$ alkyl)-$NR^{13}R^{14}$, —C(=O)$NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl;

—$(CH_2)_pOR^{13}$, —$(CH_2)_pNHR^{13}$, —$(CH_2)_pCONHR^{13}$, —$(CH_2)_pSO_2NHR^{13}$, —$(CH_2)_nOCONHR^{13}$, —$(CH_2)_pNHCONHR^{13}$, —$(CH_2)_pC(=NH)NHR^{13}$;

—C(=O)C($R^{11}$)$_2NR^{13}R^{14}$;
—C(=O)C($R^{11}$)$_2NR^{13}CO_2R^{13}$;
—C(=O)C($R^{11}$)$_2NR^{13}CO_2R^{13}$; —C(=O)-($C_1$–$C_4$alkyl) —$NR^{13}R^{14}$; —C(=O)-($C_1$–$C_4$ alkyl)—$NR^{13}CO_2R^{13}$;

$C_1$–$C_4$ alkoxy substituted with 0–4 groups selected from: $R^{11}$, $C_3$–$C_6$ cycloalkyl, —$CO_2R^{13}$, —C(=O)$NR^{13}R^{14}$, or —$NR^{13}R^{14}$;

$C_1$–$C_4$ alkyl substituted with 0–4 groups selected from: $R^{11}$, =$NR^{14}$, =$NNR^{13}C$(=O)$NR^{13}R^{14}$, or —$NR^{13}R^{14}$;

$C_2$–$C_4$ alkenyl substituted with 0–$R^{11}$, $C_2$–$C_4$ alkynyl substituted with 0–3 $R^{11}$; and a 5- or 6-membered heterocyclic ring containing from 1 to 4 heteroatoms independently selected from oxygen, nitrogen or sulfur, substituted with 0–2 $R^{12}$; and $R^{32}$, when a substituent on nitrogen, is independently selected at each occurrence from the group consisting of:

phenyl, benzyl, phenethyl, hydroxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, $C_1$–$C_4$ alkylcarbonyloxy, and $C_1$–$C_4$ alkylcarbonyl.

More preferred in the present invention is a process as described above wherein:

$R^4$ and $R^7$ are independently selected from:

$C_1$–$C_8$ alkyl substituted with 0–2 $R^{11}$;

$R^{11}$ is independently selected at each occurrence from the group consisting of:

H, halogen, —$OR^{13}$, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl)- substituted with 0–2 $R^{12}$; aryl substituted with 0–2 $R^{12}$; and a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{11A}$ is independently selected at each occurrence from the group consisting of:

H, halogen, —$OR^{13A}$, $C_3$–$C_{10}$ cycloalkyl substituted with 0–2 $R^{12A}$, $C_1$–$C_4$ alkyl substitued with 0–2 $R^{12A}$, aryl($C_1$–$C_3$ alkyl)- substituted with 0–2 $R^{12A}$, aryl substituted with 0–2 $R^{12}A$;

$NO_2$, cyano, $C_1$–$C_6$ alkyl, or phenyl, said phenyl being optionally substituted with Cl, F, Br, CN, $NO_2$, $CF_3$, $OCH_3$ or OH; and a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is independently selected at each occurrence from the group consisting of:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, —$S(O)_mMe$, $CF_3$, 2-(1-morpholino)ethoxy, hydroxamic acid, hydrazide, —$C(R^{14})$=$N(OR^{14})$, and sulfonamide;

$R^{12}$, when a substituent on nitrogen, is methyl;

$R^{12A}$, when a substituent on carbon, is independently selected at each occurrence from the group consisting of:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_mMe$, $CF_3$, 2-(1-morpholino)ethoxy, —$CO_2H$, hydroxamic acid, hydrazide, —$C(R^{14A})$=$N(OR^{14A})$, and sulfonamide;

$R^{12A}$, when a substituent on nitrogen, is independently selected at each occurrence from the group consisting of:

benzyl and methyl;

$R^{13}$ is independently selected at each occurrence from the group consisting of:

a heterocycle selected from the group consisting of:

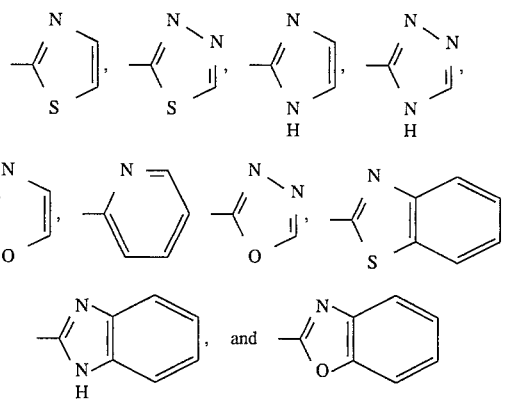

said heterocycle substituted with 0–1 $R^{11A}$ and 0–1 $R^{16}$;

H, $C_1$–$C_4$ alkyl, $C_2$–$C_4$ alkenyl, benzyl, an amine protecting group when $R^{13}$ is bonded to N, and a hydroxyl or carboxyl protecting group when $R^{13}$ is bonded to O;

$R^{14}$ is independently selected from the group consisting of:

hydrogen, $CF_3$, $C_1$–$C_4$ alkyl, $C_1$–$C_4$ alkoxy, $C_2$–$C_4$ alkenyl, benzyl, an amine protecting group when $R^{14}$ is bonded to N, and a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ or alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{22}$ and $R^{23}$ are independently selected at each occurrence from the group consisting of:

$C_1$–$C_8$ alkyl substituted with 0–2 $R^{31}$;

$C_2$–$C_6$ alkenyl substituted with 0–2 $R^{31}$; phenyl substituted with 0–2 $R^{31}$ and 0–2 $R^{32}$; and a heterocycle selected from the group consisting of thiazole, indazole, thieno[2,3-c]pyrazole and thieno[3,2-c]pyrazole, said heterocycles substituted with 0–2 $R^{31}$;

$R^{31}$ is independently selected at each occurrence from the group consisting of:

—OH, —$OCH_3$, cyano, nitro, $CF_3$, $C_1$–$C_4$ haloalkoxy. —$CO_2R^{15}$, —$COR^{15}$, halogen, —$OR^{13}$, $C_1$–$C_4$ alkyl, $C_3$–$C_{10}$ cycloalkyl, —$CO_2R^{13}$, —$S(O)_mR^{13}$;

aryl substituted with 0–3 $R^{32}$; and a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is independently selected at each occurrence from the group consisting of:

—$(CH_2)_pOR^{13}$, —$(CH_2)_pCONHR^{13}$, —$(CH_2)_nOCONHR^{13}$, —$(CH_2)_pNHCONHR^{13}$; —$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})$=$N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —OCONHCH$_2$C$_6$H$_5$, —OCONHCH$_3$, oxazolidinyl, —C≡C—CH$_2$OH, —COCH$_3$, hydroxyethyl, C$_1$–C$_3$ alkyl (said alkyl substituted with 0–4 halogen, or OH), tetrazolyl, —OCH$_2$CONH$_2$, —CONHNH$_2$, —CH=NNHCONH$_2$, —CONHOCH$_3$, —CH$_2$CH(OH)CH$_2$OH, adamantamido, hydroxyethoxy, dihydroxyethyl, —C(NH$_2$)=NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, —NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOCH(CH$_3$)NH$_2$, —NHCOCH(CH$_2$C$_6$H$_5$)NH$_2$, —CO$_2$CH$_2$CH$_3$, —CONHCH$_2$CH$_2$CH$_3$, —CONHCH(CH$_3$)$_2$, —CH$_2$-imidazole, —COC(CH$_3$)$_3$, —CH(OH)CF$_3$, —CO—imidazole, —CO—pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)=N(OH), —C(CF$_3$)=N(OH), phenyl, acetoxy, hydroxyamino, —N(CH$_3$) (CHO), cyclopropylmethoxy, —CONR$^{13}$R$^{14}$, —CONHOH, (diethylaminoethyl)aminocarbonyl, (N-ethyl,N-methylaminoethyl)aminocarbonyl, (4-methylpiperazinylethyl)aminocarbonyl, (pyrrolidinylethyl)aminocarbonyl, (piperidinylethyl)aminocarbonyl, —NHCOCH$_2$NHCH$_3$, N-(2-(4 -morpholino)ethyl)aminocarbonyl, and N-(2 -(N,N-dimethylamino)ethyl)aminocarbonyl;

p is 0; and

R$^{32}$, when a substituent on nitrogen, is independently selected at each occurrence from the group consisting of: benzyl and methyl.

Most preferred in the present invention is a process as described above wherein:

R$^4$ and R$^7$ are independently C$_1$–C$_3$ alkyl substituted with 0–1 R$^{11}$;

R$^{12A}$, when a substituent on nitrogen, is methyl;

R$^{13}$ is independently selected from the group consisting of:

a heterocycle selected from the group consisting of:

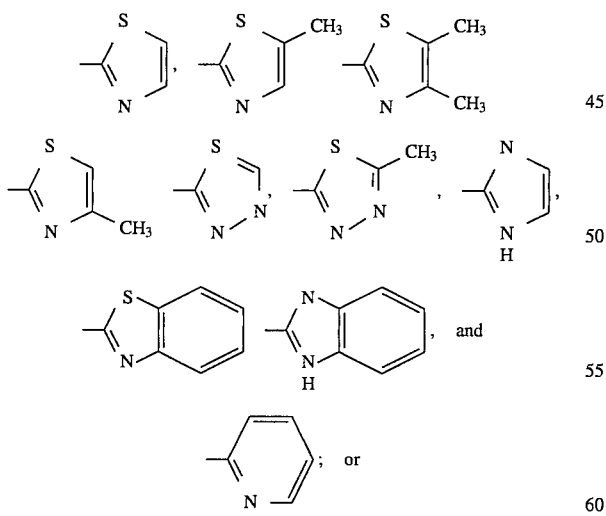

H, C$_1$–C$_4$ alkyl, C$_2$–C$_4$ alkenyl, benzyl, an amine protecting group when R$^{13}$ is bonded to N, and a hydroxyl or carboxyl protecting group when R$^{13}$ is bonded to O; R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{13A}$ and R$^{14A}$ are independently selected from: H or C$_1$–C$_6$ alkyl;

R$^{13A}$ and R$^{14A}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{15}$ is H or CH$_3$;

R$^{22}$ and R$^{23}$ are independently selected from the group consisting of:

C$_1$–C$_8$ alkyl substituted with 0–2 R$^{31}$; benzyl substituted with 0–2 R$^{31}$ and 0–2 R$^{32}$; and a heterocycle selected from the group consisting of thiazole, indazole, thieno[2,3-c]pyrazole and thieno[3,2-c]pyrazole, said heterocycle substituted with 0–2 R$^{31}$;

R$^{32}$, when a substituent on carbon, is independently selected from the group consisting of:

—(CH$_2$)$_p$OR$^{13}$, —(CH$_2$)$_p$CONHR$^{13}$, —CONH$_2$, —CO$_2$H, —CHO, —CH$_2$NHOH, —CH$_2$NR$^{13}$R$^{14}$, —NR$^{13}$R$^{14}$, hydroxy, hydroxymethyl, —C(R$^{14}$)=N(OR$^{14}$), halogen, methoxy, methyl, nitro, cyano, allyloxy, —CO$_2$CH$_3$, —NHCHO, —NHCOCH$_3$, —OCO$_2$CH$_3$, —CH=NCH$_2$CH$_2$OH, —OCONHCH$_2$C$_6$H$_5$, —OCONHCH$_3$, oxazolidinyl, —C≡C—CH$_2$OH, —COCH$_3$, hydroxyethyl, C$_1$–C$_3$ alkyl (said alkyl substituted with 0–4 halogen, or OH), tetrazolyl, —OCH$_2$CONH$_2$, —CONHNH$_2$, —CH=NNHCONH$_2$, —CONHOCH$_3$, —CH$_2$CH(OH)CH$_2$OH, adamantamido, hydroxyethoxy, dihydroxyethyl, —C(NH$_2$)=NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, —NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOCH(CH$_3$)NH$_2$, —NHCOCH(CH$_2$C$_6$H$_5$)NH$_2$, —CO$_2$CH$_2$CH$_3$, —CONHCH$_2$CH$_2$CH$_3$, —CONHCH(CH$_3$)$_2$, —CH$_2$-imidazole, —COC(CH$_3$)$_3$, —CH(OH)CF$_3$, —CO-imidazole, —CO—pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)=N(OH), —C(CF$_3$)=N(OH), phenyl, acetoxy, hydroxyamino, —N(CH$_3$) (CHO) , cyclopropylmethoxy, —CONR$^{13}$R$^{14}$, —CONHOH, (diethylaminoethyl)aminocarbonyl, (N-ethyl, N-methylaminoethyl)aminocarbonyl, (4-methylpiperazinylethyl)aminocarbonyl, (pyrrolidinylethyl)aminocarbonyl, (piperidinylethyl)aminocarbonyl, —NHCOCH$_2$NHCH$_3$, N-(2-(4 -morpholino)ethyl)aminocarbonyl, and N-(2 -(N,N-dimethylamino)ethyl)aminocarbonyl;

p is 0; and

R$^{32}$, when a substituent on nitrogen, is methyl,

Specifically preferred in the present invention is a process as described above wherein:

R$^4$ and R$^7$ are independently selected from the group consisting of:

benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl, thiomethylbenzyl, thiazolylmethyl, 3,4-methylenedioxybenzyl, and N,N-dimethylaminobenzyl;

R$^{22}$ and R$^{23}$ are independently selected from the group consisting of:

allyl, methyl, ethyl, propyl, cyclopropyl, cyclopropylmethyl, cyclobutylmethyl, n-butyl, i-butyl, CH₂CH=C(CH₃)₂, pyridylmethyl, pyridyl, methallyl, n-pentyl, i-pentyl, hexyl, phenyl, benzyl, isoprenyl, propargylmethyl, picolinylmethyl, methoxymethyl, cyclohexylmethyl, dimethylbutyl, ethoxymethyl, napthylmethyl, methyloxazolinylmethyl, naphthyl, methyloxazolinyl, vinyloxymethyl, pentafluorobenzyl, quinolinylmethyl, carboxybenzyl, chlorothienylmethyl, benzyloxybenzyl, biphenylmethyl, phenylbenzyl, adamantylmethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutyl, formaldoximebenzyl, cyclopentyl, cyclopentylmethyl, nitrobenzyl, (H₂NC(=O))-benzyl, carbomethoxybenzyl, carboethoxybenzyl, tetrazolylbenzyl, dimethylallyl, aminomethylbenzyl, (O-benzyl-formaldoxime)benzyl, (O-methyl-formaldoxime)benzyl, (CH₃O₂CO)-benzyl, (HOCH₂CH₂N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH₃C(=NOH))-benzyl, (H₂NNHC(=O))-benzyl, (H₂NC(=O)NHN=CH)-benzyl, (CH₃ONHC(=O))-benzyl, (HONHC(=O))-benzyl, (CH₃NHC(=O))-benzyl, N,N-dimethylaminocarbonylbenzyl, (HOCH₂CH(OH)CH₂O)-benzyl, hydroxyethoxybenzyl (oxazolidinyl)-benzyl, (hydroxy)pentyl, pentenyl, (hydroxy)heptyl, (hydroxy)butyl, (carboxy)butyl, (carbomethoxy)butyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH₃CH₂NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,-N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H₂NSO₂)-benzyl, dihydroxyethylbenzyl, (MeHNC(=O)NH)-benzyl, (H₂NC(=O) NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH₃CH₂C(=NOH))benzyl, (trifluorohydroxyethyl)benzyl, (CF₃C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH₃NHC(=O)O)benzyl, (NH₂C(=O)CH₂O)benzyl, (NH₂C(=NH)benzyl, ((N-phenylmethoxycarbonyl)glycylamino)benzyl, (imidazolylmethyl)benzyl, ((CH₃)₃C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl, (H₂NC(=NOH))benzyl, (H₂NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl, N-butylaminobenzyl, N,N-dimethylaminobenzyl, N-propylaminobenzyl, N-methylaminomethylbenzyl, carbomethoxybenzyl, N-methylaminocarbonylbenzyl,glycylaminobenzyl, N,N-dimethylaminocarbonylbenzyl, N,N-diethylaminobenzyl, alanylaminobenzyl, phenylalanylaminobenzyl, (N-methylglycyl)aminobenzyl, (H₂NC(=NOH))benzyl, (CH₃C(=NOH))benzyl, 2-amino-5-benzoxazolylmethyl, 3-amino-5-benzisoxazolylmethyl, 3-amino-5-indazolylmethyl, 3-methylamino- 5-indazolylmethyl, 3-ethylamino-5-indazolylmethyl, 3-methyl-5-indazolylmethyl, 3-ethyl- 5-indazolylmethyl, 3-methoxy-5-indazolylmethyl, 3-methoxycarbonyl-5-indazolylmethyl, 3-chloro-5-indazolylmethyl, 3,4-methylenedioxybenzyl, pyridylmethyl, 3 -(2-thiazolylaminocarbonyl)benzyl, 3-(4 -methyl-2-thiazolylaminocarbonyl)benzyl, 3- (1,3,4-thiadiazol-2-ylaminocarbonyl)benzyl, 3-(5-methyl-1,3,4-thiadiazol-2-ylaminocarbonyl)benzyl, 3-(5 -t-butyl-1,3,4-thiadiazol-2-ylaminocarbonyl)benzyl, 3-(5-methyl-2-thiazolylaminocarbonyl)benzyl, 3-(4,5-dimethyl-2-thiazolylaminocarbonyl)benzyl, 3-(2-imidazolylaminocarbonyl)benzyl, 3-(2-pyridylaminocarbonyl)benzyl, 3-(2-benzothiazolylaminocarbonyl)benzyl, 3-(2-benzimidazolylaminocarbonyl)benzyl, 3-(2-thiazolyloxy)benzyl, and 3-(2-pyridinyloxy)benzyl.

Synthesis

The disclosures of all of the references cited herein are hereby incorporated herein by reference in their entirety.

Using the procedures described above and outlined in Schemes 6 and 7, the following compounds were prepared. The following examples are meant to be illustrative of the present invention. These examples are not to be construed as limiting the invention's scope. With a judicious selection of reagents, as is well appreciated to one skilled in the art, these manipulations can be performed in a straightforward manner to yield the claimed combinations for compounds of the invention.

EXAMPLE 1

Synthesis of compound (I): $R^4$, $R^7$=benzyl; $R^5$, $R^6$=TES

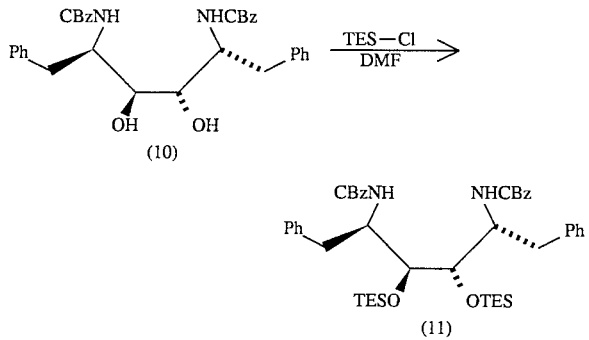

PART A: Imidazole (11 kg, 161.6 moles) was dissolved in N,N'-dimethylformamide (43.1 kg, 45.4 L). Triethylchlorosilane (20.4 kg, 135.4 moles, TES-Cl) was added at such a rate that the temperature was maintained below 15° C. Compound (10) (30 kg, 52.8 moles) was added in 10 charges of 3 kg each. The charges were done at such a rate that temperature was below 15° C. After the addition was complete the reaction mixture was heated to 35° C. Reaction was complete after 12 hours. Toluene (39.3 kg, 45 L) was added and then 47 L of USP water. Celite (3.1 kg) was added and the mixture was filtered through a 0.5 micron bag filter. Layers were separated and the top organic layer was washed with water (2×45 L). The resulting toluene layer was dried by distillation in vacuo of 18 L of the toluene-water azeotrope. Dry toluene (18 L) was added to bring the volume back to the original level. This solution was divided into two identical fractions, which were hydrogenated and cyclized under identical conditions described below.

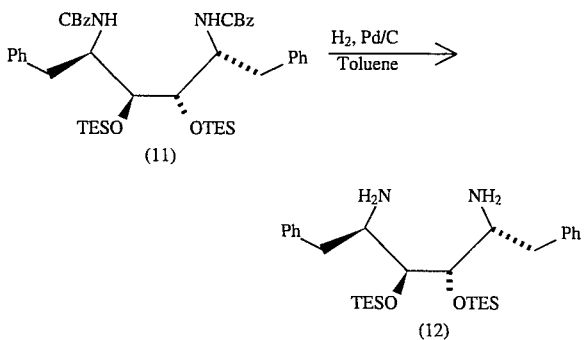

PART B: Palladium hydroxide on carbon wet (0.75 kg) was slurried into the toluene solution from Part A. Hydrogen (5 psig) was applied and the mixture was heated to 45° C. Every 15 minutes, the system was purged to help the elimination of $CO_2$ gas from the solution. Reaction was complete after 8 hours.

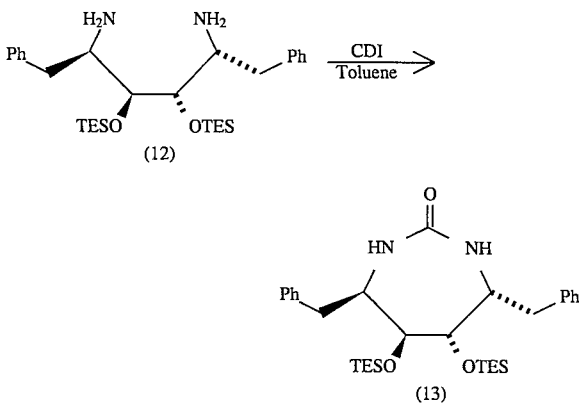

PART C: The system was purged with nitrogen and the mixture from Part B was cooled down to 20° C. 1,1'-Carbonyldiimidazole (CDI) (4.5 kg) was added and the mixture stirred for 30 minutes at 20°–22° C. An aqueous 1 N hydrochloric acid solution (34 kg) was then added and the mixture was filtered. Layers were separated and the top organic layer was washed with USP water (25 L).

EXAMPLE 2

Synthesis of compound (I): $R^5$, $R^6$=—$OCH_2OCH_2O$—; $R^4$, $R^7$=benzyl

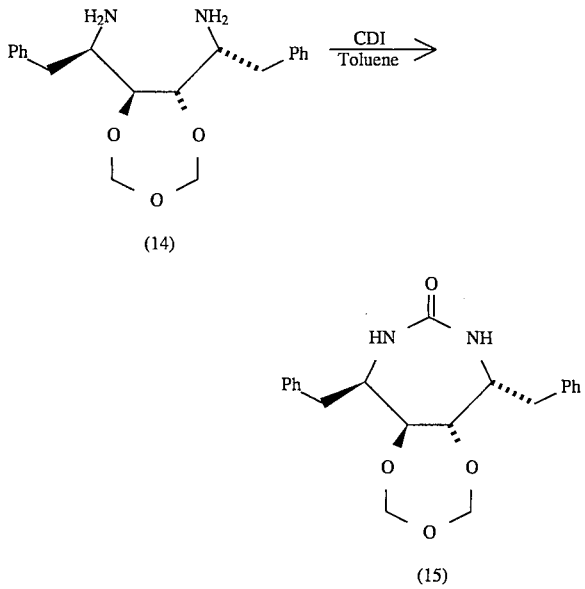

Compound (14) (100 g, 0.1375 mol) was suspended in acetonitrile (1 L) and triethylamine (21.1 mL, 0.1513 mol) was added. The resulting solution was cooled to 5° C. and a solution of carbonyl diimidazole (11.15 g, 0.0688 mol) in acetonitrile (0.5 L) was added over 50 minutes. The reaction was then warmed to room temperature and held for one hour. Carbonyl diimidazole (5.6 g, 0.0344 mol) was added as a solid and the reaction stirred for one hour. Another charge of carbonyl diimidazole (5.6 g, 0.0344 mol) was added as a solid and the reaction stirred another hour. A final charge of solid carbonyl diimidazole (3.3 g, 0.0204 mol) was added and the reaction was stirred overnight. 4-Methyl-2-pentanone (1 L) and 1 N hydrochloric acid (0.5 L) were added and the layers were separated. The organic layer was washed with additional 1 N hydrochloric acid (0.5 L) and the layers separated. The combined aqueous layers were back extracted with 4-methyl-2-pentanone (2×0.3 L). The combined organic layers were reduced to 1.5 L and then washed first with brine (0.5 L) then with 8% sodium bicarbonate (0.5 L). The organic layer was reduced to 0.3 L then hexanes (1 L) were added. The resulting slurry was cooled in an ice bath for 1.5 h, then filtered and rinsed with cold hexanes (100 mL). The white solid compound (15) was dried under vacuum at 90° C. to give 46.66 g (83%), mp 125°–130° C.

EXAMPLE 3

Synthesis of Compound (II): $R^4$, $R^7$=benzyl; $R^5$, $R^6$=—OC(CH$_3$)$_2$O—; $R^1$=CH$_3$.

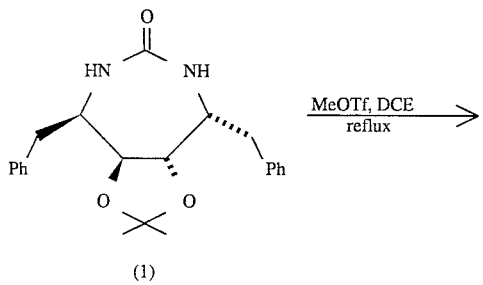

(1)

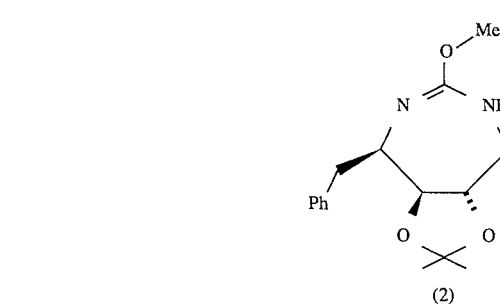

(2)

To a suspension of compound (1) (10.0 g; 27.3 mmol) in 1,2-dichloroethane (100 mL) was added methyltriflate (3.4 mL, 30 mmol). After refluxing overnight, the reaction was washed with sat. NaHCO$_3$, sat. NaCl, dried (Na$_2$SO$_4$) and evaporated leaving 12.5 g of a yellow oil. Column chromatography (flash SiO$_2$; 25% EtOAc/hexane) gave 7.86 g of compound (2) as a pale yellow oil which crystallized on standing (75% yield). m.p.=97°–100° C. MH$^+$=381

EXAMPLE 4

Synthesis of Compound (III): $R^4$, $R^7$=benzyl; $R^5$, $R^6$=—OC(CH$_3$)$_2$O—; $R^1$=CH$_3$; $R^{23}$=—CH$_2$—(3-cyano-4-fluorophenyl).

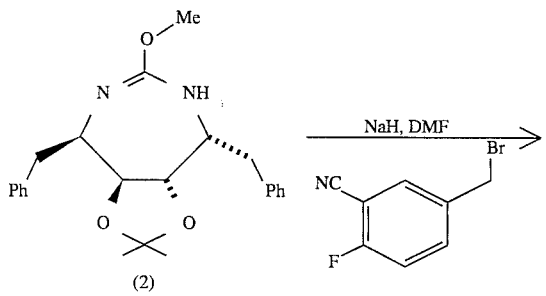

(2)

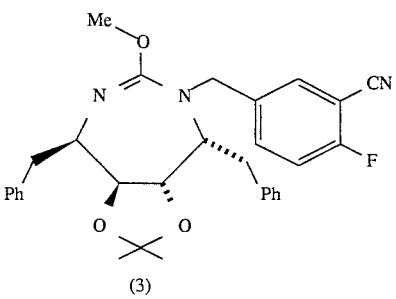

(3)

To a 0° C. solution of the isourea 2 (4.43 g; 11.7 mmol) and 3-cyano-4-fluorobenzyl bromide (5.00 g; 23.3 mmol) in DMF (50 mL), was added NaH (60% in mineral oil; 1.40 g; 35.0 mmol). After warming to room temperature and stirring overnight, the reaction was added to 25% Et$_2$O/EtOAc. The organic phase was washed with water (3×), saturated NaCl, dried (Na$_2$SO$_4$) and evaporated leaving a yellow oil. Column chromatography (flash SiO$_2$; EtOAc/hexane) gave 5.55 g of isourea 3 as a colorless oil (92% yield) MH$^+$=514.

EXAMPLE 5

Synthesis of Compound (IV): $R^4$, $R^7$=benzyl; $R^5$, $R^6$=—OC(CH$_3$)$_2$O—; $R^{23}$=—CH$_2$—(3-cyano-4-fluorophenyl); $R^{22}$=benzyl.

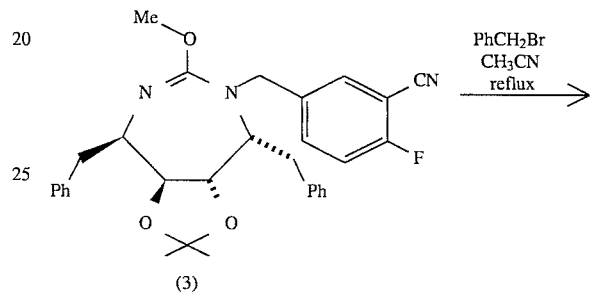

(3)

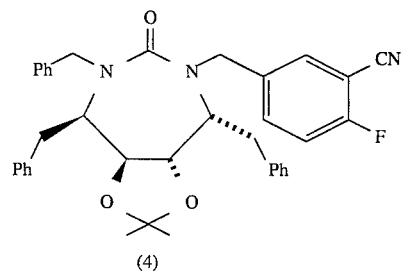

(4)

A solution of the isourea 3 (2.78 g; 5.41 mmol) and benzyl bromide (1.93 mL; 16.2 mmol) in acetonitrile (15 mL) was refluxed overnight. The reaction was evaporated and subjected to column chromatography (flash SiO$_2$; 20% EtOAc/hexane) to give 3.02 g of (4) as a white foam (95% yield). MH$^+$=590.

EXAMPLE 6

Synthesis of Compound (IV): $R^4$, $R^7$=benzyl; $R^5$, $R^6$=—OC(CH$_3$)$_2$O—; $R^{23}$=—CH$_2$—(3-aminoindazol-5-yl); $R^{22}$=benzyl.

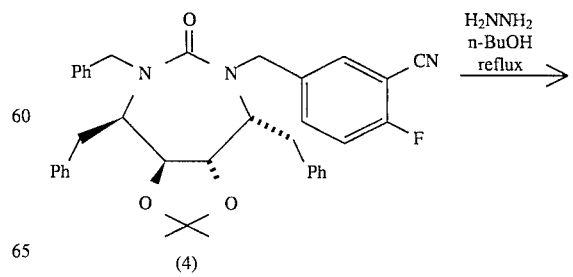

(4)

-continued

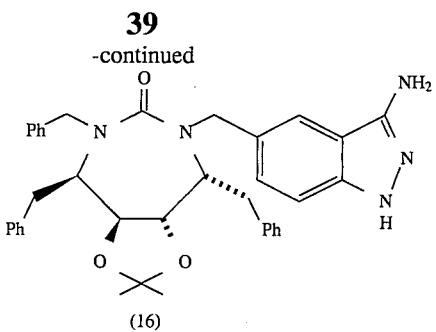

(16)

A solution of the nitrile (4) (3.02 g; 5.13 mmol) in n-BuOH (30 mL) and hydrazine hydrate (6 mL) was refluxed overnight. The reaction was added to EtOAc and washed with 10% citric acid (2×), sat. NaCl, sat. NaHCO$_3$, sat. NaCl, dried (NaSO$_4$) and evaporated leaving 3.09 g of (16) as a white foam (100% yield). MH$^+$=602

EXAMPLE 7

Synthesis of Compound (VIb): R$^4$, R$^7$=benzyl; R$^{23}$=—CH$_2$—(3-aminoindazol-5-yl); R$^{22}$=benzyl.

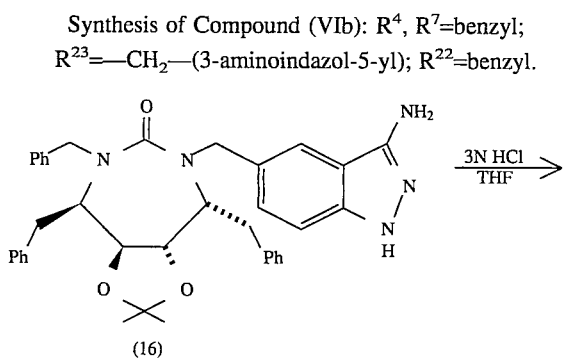

A solution of the acetonide (16) (3.09 g; 5.14 mmol) in 3 N HCl (10 mL) and THF (40 mL) was stirred overnight. The reaction was added to EtOAc and washed with sat. NaHCO$_3$, sat. NaCl, dried (NaSO$_4$) and evaporated leaving an orange oil. Column chromatography (flash SiO$_2$, 7% MeOH/CH$_2$Cl$_2$ and 0.8% NH$_4$OH) gave 2.15 g pink glassy solid. Crystallization from 3:1 CH$_2$Cl$_2$/Et$_2$O gave 1.7 g of (17) as pale pink crystals which were dried overnight under high vacuum at 85° C. mp=134°–139° C.

EXAMPLE 8

Synthesis of Compound (V): R$^4$, R$^7$=benzyl; R$^5$, R$^6$=—OC(CH$_3$)$_2$O—; R$^{23}$=—CH$_2$—(pyridin-3-yl);

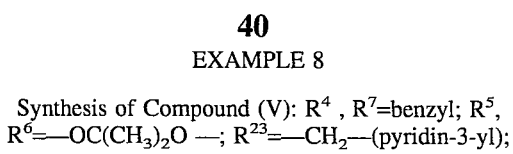

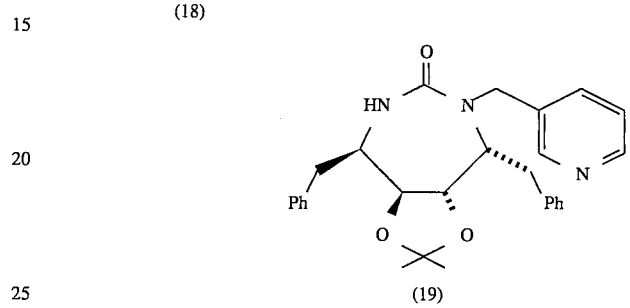

A solution of the isourea (18) (850 mg; 1.81 mmol) in EtOH (3 mL) and hydrazine hydrate (3 mL) was refluxed overnight. The reaction was added to 5:1 EtOAc/Et$_2$O and washed with water (3×), sat. NaCl (2×), dried (Na$_2$SO$_4$) and evaporated leaving 780 mg of (19) as a colorless oil (95% yield). MH$^+$=457.

EXAMPLE 9

Synthesis of Compound (II): R$^4$, R$^7$=benzyl; R$^5$, R$^6$=SEM; R$^1$=CH$_3$CH$_2$—.

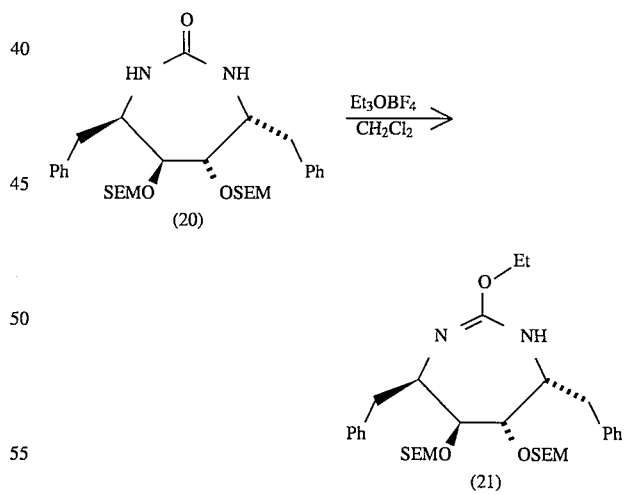

Compound (20) (0.40 g, 0.682 mmol) was added to CH$_2$Cl$_2$ (60 mL) under nitrogen and the solution chilled to −78° C. Triethyloxonium tetrafluoroborate (0.75 mL or 1.0

M solution, 0.75 mmol) was added. The reaction was allowed to warm to ambient temperature and stirred 12 hrs. The reaction solution was washed with aqueous NaHCO$_3$ (sat'd, 20 mL) and the organic layer was dried over MgSO$_4$ and evaporated to an oily residue (21). (M+H)$^+$ 615.

EXAMPLE 10

Synthesis of Compound (II): R$^4$, R$^7$=benzyl; R$^5$, R$^6$=—OC(CH$_3$)$_2$O—; R$^1$=CH$_3$—.

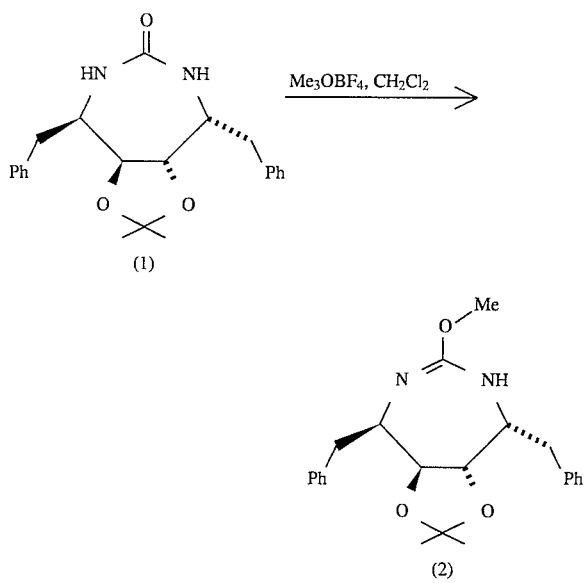

Compound (1) (1.00 g, 2.73 mmol) was dissolved in CH$_2$Cl$_2$ (25 mL), and Me$_3$OBF$_4$ (0.61 g) was added while mixing under a nitrogen blanket at ambient temperature. After 3.5 hrs, a solution of NaHCO$_3$ (1.0 g in 25 mL of water) was added. The layers were separated and the organic layered dried over Na$_2$SO$_4$ and evaporated to yield a foamy residue (2) (0.97 g). $^1$HNMR spectrum agreed with reference spectrum.

EXAMPLE 11

Synthesis of Compound (II): R$^4$, R$^7$=benzyl; R$^5$, R$^6$=MEM; R$^1$=CH$_3$CH$_2$—.

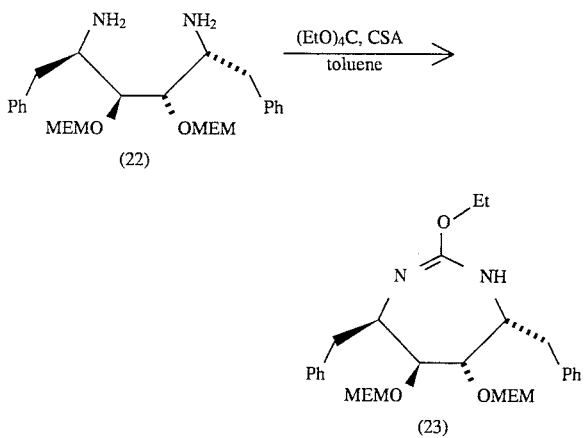

A solution of the diamine (22) (0.16 g, 0.34 mmol), tetraethyl orthocarbonate (0.32 g, 1.7 mmol) and (±)-camphorsulfonic acid (5 mg, 0.022 mmol) in 10 mL of toluene was heated to reflux overnight. After cooling to room temperature, the solvent and excess tetraethyl orthocarbonate were evaporated and dried in vacuo to give 0.19 g of a viscous liquid. The product was purified by flash column chromatography (silica gel, hexane/ethyl acetate=100:0 to 0/100) to give 80 mg (44% yield) of (23). $^1$H NMR (300 HMz, CDCl$_3$) δ7.35–7.10 (m, 10H), 4.90–4.65 (br, 4H), 4.03–3.50 (m, 10H), 3.45–3.40 (m, 4H), 3.35 (s, 6H), 2.98–2.75 (m, 4H), 0.94 (t, 3H, J=7.1 Hz). MS (NH$_3$/DCI) 531 (M+H, 100). HRMS calcd for C$_{29}$H$_{43}$N$_2$O$_7$ (M+H) 531.3070, found 531.3052.

Utility

The compounds of this invention possess retroviral protease inhibitory activity, in particular, HIV inhibitory efficacy, as evidenced by their activity in the assays, as described in Lam et al., PCT International Publication Number WO 93/07,128, EP 402646 A1, and copending commonly assigned U.S. patent application Ser. No. 08/197,630, filed Feb. 16, 1994. The compounds of formulae (VIa) and (VIb) possess HIV protease inhibitory activity and are therefore useful as antiviral agents for the treatment of HIV infection and associated diseases as demonstrated by their in vivo efficacy in mammals. The compounds of formulae (via) and (VIb) possess HIV protease inhibitory activity and are effective as inhibitors of HIV growth.

Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

The compounds of the present invention are also useful for the inhibition of HIV in an ex vivo sample containing, or suspected of containing, HIV. The compounds according to the invention can be used to treat body fluid samples. Thus, the compounds of the present invention can be used to inhibit HIV present in, for example, a serum or semen sample which contains, or is suspected of containing, HIV. The samples can be treated, for example, in a method similar to those described in the specification for the "HIV Yield Reduction Cell Assay" (page 163) and the "HIV Low Multiplicity Assay" of copending commonly assigned U.S. patent application Ser. No. 08/197,630 filed Feb. 16, 1994.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

We claim:

1. A process for the preparation of a compound of the formula (VIb):

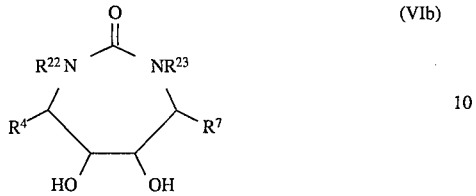

or pharmaceutically acceptable salts or prodrug forms thereof wherein:

$R^4$ and $R^7$ are the same and are selected from the group consisting of:
$C_1$–$C_8$ alkyl substituted with 0–3 $R^{11}$; $C_2$–$C_8$ alkenyl substituted with 0–3 $R^{11}$; and $C_2$–$C_8$ alkynyl substituted with 0–3 $R^{11}$;

$R^{11}$ is independently selected at each occurrence from the group consisting of;
H, keto, halogen, cyano, —$CH_2NR^{13}R^{14}$, —$NR^{13}R^{14}$, —$CO_2R^{13}$, —$OC(=O)R^{13}$, —$OR^{13}$, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, —$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)(OR^{13})_2$, $C_1$–$C_4$ alkyl, $C_2$–$C_4$ alkenyl, $C_3$–$C_6$ cycloalkylmethyl, phenyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino)ethoxy, azido, —$C(R^{14})=N(OR^{14})$;

$C_3$–$C_{10}$ cycloalkyl substituted with 0–2 $R^{12}$;
$C_1$–$C_4$ alkyl substitued with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
$C_1$–$C_4$ alkylcarbonyloxy substituted with 0–2 $R^{12}$;
$C_6$–$C_{10}$ arylcarbonyloxy substituted with 0–2 $R^{12}$;
a $C_5$–$C_{14}$ carbocyclic residue substituted with 0–3 $R^{12}$; and
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is independently selected at each occurrence from the group consisting of;
H, keto, halogen, cyano, —$CH_2N(R^{13A})R^{(14A)}$, —$OR^{13A}$ —$N(R^{13A})R^{(14A)}$, —$CO_2H$, —$OC(=O)$ ($C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl($C_1$–$C_3$ alkyl);
$C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)-substituted with 0–2 $R^{12A}$;
a 5- to 10-membered heterocyclic ring system containing 1 to 4 heteroatoms independently selected from oxygen, nitrogen or sulfur, said heterocyclic ring system substituted with 0–3 $R^{12A}$;
—$SO_mR^{13A}$, $C_1$–$C_4$ haloalkyl, $C_1$–$C_4$ haloalkoxy, $C_1$–$C_4$ alkoxy, $C_2$–$C_4$ alkynyl, phenyl, said phenyl being optionally substituted with Cl, F, Br, CN, $NO_2$, $CF_3$, $C_1$–$C_4$ alkyl, $C_1$–$C_4$ alkoxy or OH; and $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy, $NH_2$ or OH;

$R^{12}$, when a substituent on carbon, is independently selected at each occurrence from the group consisting of;
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, —$NR^{13}R^{14}$, $C_1$–$C_4$ alkyl substituted with —$NR^{13}R^{14}$, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$;
a 5- or 6-membered heterocyclic ring containing from 1 to 4 heteroatoms independently selected from oxygen, nitrogen or sulfur;
or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; and
when $R^{12}$ is attached to a saturated carbon atom, it may be =O or =S; or when $R^{12}$ is attached to sulfur it may be =O.

$R^{12}$, when a substituent on nitrogen, is independently selected at each occurrence from the group consisting of;
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, and —$C(R^{14})=N(OR^{14})$;

$R^{12A}$, when a substituent on carbon, is independently selected at each occurrence from the group consisting of;
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13A}$, $C_1$–$C_4$ alkyl substituted with —$NH_2$, —$NH_2$, —NHMe, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mMe$, —$SO_2NH_2$, —$NHSO_2Me$, —$OCH_2CO_2R^{13A}$, 2-(1-morpholino)ethoxy;

a 5- or 6-membered heterocyclic ring containing from 1 to 4 heteroatoms independently selected from oxygen, nitrogen or sulfur;

$R^{12A}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NH_2$; and when $R^{12A}$ is attached to a saturated carbon atom, it may be =O or =S; or when $R^{12A}$ is attached to sulfur it may be =O.

$R^{12A}$, when a substituent on nitrogen, is independently selected at each occurrence from the group consisting of;

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, and $C_1$–$C_4$ alkylcarbonyl;

$R^{13}$ is independently selected at each occurrence from the group consisting of;

H; heterocycle substituted with 0–3 $R^{11A}$ and 0–1 $R^{16}$; phenyl substituted with 0–3 $R^{11A}$; benzyl substituted with 0–3 $R^{11A}$; $C_1$–$C_6$ alkyl substituted with 0–3 $R^{11A}$; $C_2$–$C_4$ alkenyl substituted with 0–3 $R^{11A}$; $C_1$–$C_6$ alkylcarbonyl substituted with 0–3 $R^{11A}$; $C_1$–$C_6$ alkoxycarbonyl substituted with 0–3 $R^{11A}$; $C_1$–$C_6$ alkylaminocarbonyl substituted with 0–3 $R^{11A}$; $C_3$–$C_6$ alkoxyalkyl substituted with 0–3 $R^{11A}$; an amine protecting group when $R^{13}$ is bonded to N; and a hydroxyl protecting group when $R^{13}$ is bonded to O;

$R^{14}$ is independently selected at each occurrence from the group consisting of;

hydrogen, $C_1$–$C_6$ alkoxy, $C_2$–$C_6$ alkenyl, phenyl, benzyl, an amine protecting group when $R^{14}$ is bonded to N, a hydroxyl or carboxyl protecting group when $R^{14}$ is bonded to O; and $C_1$–$C_6$ alkyl substituted with 0–3 groups selected from OH, $C_1$–$C_4$ alkoxy, halogen, $R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14}$ are independently selected at each occurrence from the group consisting of:

H and $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, —CN, —$NO_2$, $C_1$–$C_4$ haloalkyl, $C_1$–$C_4$ haloalkoxy, $C_1$–$C_4$ alkoxy, $C_1$–$C_6$ alkyl, $C_2$–$C_4$ alkenyl, $C_2$–$C_4$ alkynyl, phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, CN, $NO_2$, $CF_3$, $C_1$–$C_4$ alkyl, $C_1$–$C_4$ alkoxy or OH; or $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

m is 0, 1 or 2;

$R^{22}$ and $R^{23}$ are independently selected at each occurrence from the group consisting of;

$C_1$–$C_8$ alkyl substituted with 0–3 $R^{31}$; $C_2$–$C_8$ alkenyl substituted with 0–3 $R^{31}$; $C_2$–$C_8$ alkynyl substituted with 0–3 $R^{31}$; a $C_3$–$C_{14}$ carbocyclic ring system substituted with 0–5 $R^{31}$ and 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is independently selected at each occurrence from the group consisting of;

—OH, $C_1$–$C_4$ alkoxy, —$CO_2R^{15}$, —$COR^{15}$, keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —NHC(=NH)$NHR^{13}$, —C(=NH)$NHR^{13}$, —C(=O)$NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{13}C(=S)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$;

a $C_5$–$C_{14}$ carbocyclic residue substituted with 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is independently selected at each occurrence from the group consisting of:

phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, sulfonamide, —CHO, $C_3$–$C_6$ cycloalkoxy, —$NR^{13}R^{14}$, —$C(R^{14})=N(OR^{14})$, —$NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$B(OH)_2$, —$OCO_2R^{13}$, phenyl, —C(=O)NR¹³—(C₁-C₄ alkyl)—NR¹³R¹⁴,
—C(=O)NR⁴⁰R⁴¹, C₁-C₄ haloalkyl, C₁-C₄ haloalkoxy, C₂-C₄ haloalkenyl, C₁-C₄ haloalkynyl;
—C(=O)NR¹³C(R¹¹)₂NR¹³R¹⁴,
—C(=O)NR¹³C(R¹¹)₂NR¹³CO₂R¹³,
—C(=O)NR¹³—(C₁-C₄ alkyl)—NR¹³CO₂R¹³,
—C(=O)N(R¹³)—(C₁-C₄ alkyl)—R¹¹,
—C(=O)C(R¹¹)₂NR¹³R¹⁴,
—C(=O)C(R¹¹)₂NR¹³CO₂R¹³, —C(=O)—(C₁-C₄ alkyl)—NR¹³R¹⁴, —C(=O)—(C₁-C₄ alkyl)—NR¹³CO₂R¹³;
—(CH₂)ₚOR¹³, —(CH₂)ₚNHR¹³, —(CH₂)ₚCONHR¹³, —(CH₂)ₚSO₂NHR¹³, —(CH₂)ₙNHCOR¹³, —(CH₂)ₚNHCO₂R¹³, —(CH₂)ₙOCONHR¹³, —(CH₂)ₚNHCONHR¹³, —(CH₂)ₚC(=NH)NHR¹³;
C₁-C₄ alkoxy substituted with 0–4 groups selected from: R¹¹, C₃-C₆ cycloalkyl, —CO₂R¹³, —C(=O)NR¹³R¹⁴, —NR¹³R¹⁴ or OH;
C₁-C₄ alkyl substituted with 0–4 groups selected from: R¹¹, =NR¹⁴, =NNR¹³C(=O)NR¹³R¹⁴, =NNR¹³C(=O)OR¹³, or —NR¹³R¹⁴;
C₂-C₄ alkenyl substituted with 0–4 R¹¹, C₂-C₄ alkynyl substituted with 0–4 R¹¹;
a 5- or 6-membered heterocyclic ring containing from 1 to 4 heteroatoms independently selected from oxygen, nitrogen or sulfur, substituted with 0–2 R¹²;
R³² may be a 3- or 4- carbon chain attached to adjacent carbons on the ring to form a fused 5- or 6-membered ring, said 5- or 6- membered ring being optionally substituted on the aliphatic carbons with halogen, C₁-C₄ alkyl, C₁-C₄ alkoxy, hydroxy, or —NR¹³R¹⁴;
when R³² is attached to a saturated carbon, it may be =O, =S, =NOH; and
when R³² is attached to sulfur it may be =O;
p is 0, 1, or 2
n is 1 or 2;
R³², when a substituent on nitrogen, is independently selected at each occurrence from the group consisting of;
phenyl, benzyl, phenethyl, hydroxy, C₁-C₄ hydroxyalkyl, C₁-C₄ alkoxy, C₁-C₄ alkyl, C₃-C₆ cycloalkyl, C₃-C₆ cycloalkylmethyl, —CH₂NR¹³R¹⁴, —NR¹³R¹⁴, C₂-C₆ alkoxyalkyl, C₁-C₄ haloalkyl, C₁-C₄ alkoxycarbonyl, C₁-C₄ alkylcarbonyloxy, C₁-C₄ alkylcarbonyl, and —C(R¹⁴)=N(OR¹⁴);
R⁴⁰ is selected from: H or C₁-C₃ alkyl; and
R⁴¹ is selected from:
—C(=O)NR¹³R¹⁴; —C(=O)NR¹³NR¹³R¹⁴;
—C(=O)C(R¹¹)₂NR¹³R¹⁴;
—C(=O)C(R¹¹)₂NR¹³NR¹³R¹⁴;
—C(=O)C(R¹¹)₂NR¹³CO₂R¹³; —C(=O)H;
—C(=O)R¹¹; —C(=O)—(C₁-C₄ alkyl)—NR¹³R¹⁴; —C(=O)—(C₁-C₄ alkyl)—NR¹³CO₂R¹³; or
1–3 amino acids linked together via amide bonds, and linked to the N atom via the carboxylate terminus; and
all functional groups, such as amines, carboxyls, ketones, aldehydes, hydrazines, guanidines, hydroxamino acids, alcohols, oximes, and thiols, that are reactive with the chemistry of this process are protected in such a form that the protecting groups may be kept or removed;
said process comprising the steps of:

step (3a): contacting a compound of the formula (II)

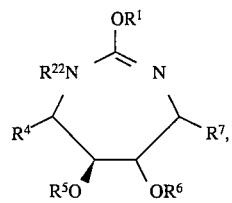
(III)

wherein:

R¹ is methyl or ethyl;

R⁵ and R⁶ are the same and are selected from the group consisting of:
C₁-C₆ alkyl substituted with 0–3 R¹¹; C₃-C₆ alkoxyalkyl substituted with 0–3 R¹¹; C₁-C₆ alkylcarbonyl substituted with 0–3 R¹¹; C₁-C₆ alkoxycarbonyl substituted with 0–3 R¹¹; C₁-C₆ alkylaminocarbonyl substituted with 0–3 R¹¹; benzoyl substituted with 0–3 R₁₂; phenoxycarbonyl substituted with 0–3 R¹²; phenylaminocarbonyl substituted with 0–3 R¹²; a hydroxyl protecting; and
any group that, when administered to a mammalian subject, cleaves to form a free hydroxyl group; or R⁵ and R⁶ may alternatively be taken together, along with the oxygen atoms to which they are attached, to form a group selected from the group consisting of:
—O—C—(CH₂CH₂CH₂CH₂CH₂—)—O—,
—O—C(CH₂CH₃)₂—O—,
—O—C(CH₃)(CH₂CH₃)—O—,
—O—C(CH₂CH₂CH₂CH₃)₂—O—,
—O—C(CH₃)(CH₂CH(CH₃)CH₃)—O—,
—O—CH(phenyl)—O—, —OCH₂SCH₂O—,
—OCH₂OCH₂O—, —OS(=O)O—,
—OC(=O)O—, —OCH₂O—, —OC(=S)O—,
—OS(=O)₂O—, —OC(=O)C(=O)O—,
—OC(CH₃)₂O—, and —OC(OCH₃)(CH₂CH₂CH₃)₂O—; and all other substituents are as defined above; in an aprotic solvent with at least one molar equivalent of a nitrogen alkylating agent R²³-Z, wherein Z is leaving group such as halide or sulfonate and R²³ is as defined above, for a period of time sufficient to form a compound of the formula (IV)

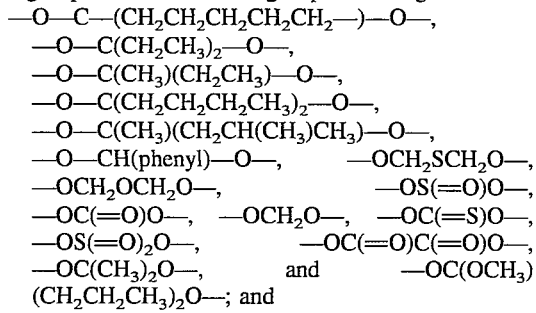
(IV)

which is optionally isolated; and step (5): contacting a compound of the formula (IV) with a reagent or condition or combination of reagents and/or conditions for a period of time sufficient to effect the removal of R⁵, R⁶ and any protecting groups and/or to convert functional groups to their desired form to form a compound of the formula (VIb) which is isolated.

2. The method of claim 1 wherein the compound of the formula (IV) is made by:

step (3c): contacting a compound of the formula (III) in a solvent with at least 2 molar equivalents of an isourea oxygen dealkylating agent for a period of time sufficient to form a compound of the formula (V)

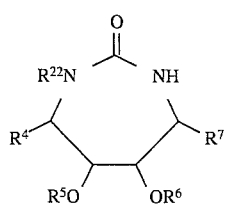

(V)

which is optionally isolated; and step (4c): contacting a compound of the formula (V) in an aprotic solvent with at least one molar equivalent of a strong base and at least one molar equivalent of a nitrogen alkylating agent $R^{23}$-Z for a period of time sufficient to form a compound of the formula (IV).

3. A process for the preparation of a compound of the formula (VIa)

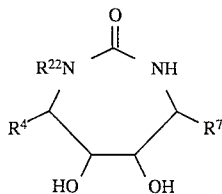

(VIa)

or pharmaceutically acceptable salts or prodrug forms thereof wherein:

$R^4$ and $R^7$ are the same and are selected from the group consisting of:

$C_1$–$C_8$ alkyl substituted with 0–3 $R^{11}$; $C_2$–$C_8$ alkenyl substituted with 0–3 $R^{11}$; and $C_2$–$C_8$ alkynyl substituted with 0–3 $R^{11}$;

$R^{11}$ is independently selected at each occurrence from the group consisting of;

H, keto, halogen, cyano, —$CH_2NR^{13}R^{14}$, —$NR^{13}R^{14}$, —$CO_2R^{13}$, —OC(=O)$R^{13}$, —$OR^{13}$, —S(O)$_mR^{13}$, —NHC(=NH)NHR$^{13}$, —C(=NH)NHR$^{13}$, —C(=O)NR$^{13}R^{14}$, —NR$^{14}$C(=O)R$^{13}$, =NOR$^{14}$, —NR$^{14}$C(=O)OR$^{14}$, —OC(=O)NR$^{13}R^{14}$, —NR$^{13}$C(=O)NR$^{13}R^{14}$, —NR$^{14}$SO$_2$NR$^{13}R^{14}$, —NR$^{14}$SO$_2R^{13}$, —SO$_2$NR$^{13}R^{14}$, —OP(O)(OR$^{13}$)$_2$, $C_1$–$C_4$ alkyl, $C_2$–$C_4$ alkenyl, $C_3$–$C_6$ cycloalkylmethyl, phenyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —NR$^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, —C(R$^{14}$)=N(OR$^{14}$); $C_3$–$C_{10}$ cycloalkyl substituted with 0–2 $R^{12}$; $C_1$–$C_4$ alkyl substitued with 0–2 $R^{12}$; aryl($C_1$–$C_3$ alkyl)-, substituted with 0–2 $R^{12}$; $C_2$–$C_6$ alkoxyalkyl-, substituted with 0–2 $R^{12}$; $C_1$–$C_4$ alkylcarbonyloxy substituted with 0–2 $R^{12}$; $C_6$–$C_{10}$ arylcarbonyloxy substituted with 0–2 $R^{12}$; a $C_5$–$C_{14}$ carbocyclic residue substituted with 0–3 $R^{12}$; and a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is independently selected at each occurrence from the group consisting of;

H, keto, halogen, cyano, —CH$_2$N(R$^{13A}$)R$_{(14A)}$, —OR$^{13A}$ —N(R$^{13A}$)R$^{(14A)}$, —CO$_2$H, —OC(=O) ($C_1$–$C_3$ alkyl), —OH, $C_2$–$C_6$ alkoxyalkyl, —C(=O)NH$_2$, —OC(=O)NH$_2$, —NHC(=O)NH$_2$, —SO$_2$NH$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —NH$_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, aryl($C_1$–$C_3$ alkyl);

$C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;

a 5- to 10-membered heterocyclic ring system containing 1 to 4 heteroatoms independently selected from oxygen, nitrogen or sulfur, said heterocyclic ring system substituted with 0–3 $R^{12A}$; —SO$_mR^{13A}$, $C_1$–$C_4$ haloalkyl, $C_1$–$C_4$ haloalkoxy, $C_1$–$C_4$ alkoxy, $C_2$–$C_4$ alkynyl, phenyl, said phenyl being optionally substituted with Cl, F, Br, CN, NO$_2$, CF$_3$, $C_1$–$C_4$ alkyl, $C_1$–$C_4$ alkoxy or OH; and $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, NO$_2$, CF$_3$, $C_1$–$C_4$ alkyl, $C_1$–$C_4$ alkoxy, NH$_2$ or OH;

$R^{12}$, when a substituent on carbon, is independently selected at each occurrence from the group consisting of;

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, hydrazide, boronic acid, sulfonamide, formyl, $C_3$–$C_6$ cycloalkoxy, —OR$^{13}$, —NR$^{13}R^{14}$, $C_1$–$C_4$ alkyl substituted with —NR$^{13}R^{14}$, $C_2$–$C_6$ alkoxyalkyl optionally substituted with —Si(CH$_3$)$_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_mR^{13}$, —SO$_2$NR$^{13}R^{14}$, —NHSO$_2R^{14}$, —OCH$_2$CO$_2R^{13}$, 2-(1-morpholino)ethoxy, —C(R$^{14}$)=N(OR$^{14}$);

a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —NR$^{13}R^{14}$; and when $R^{12}$ is attached to a saturated carbon atom, it may be =O or =S; or when $R^{12}$ is attached to sulfur it may be =O.

$R^{12}$, when a substituent on nitrogen, is independently selected at each occurrence from the group consisting of;

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}R^{14}$, —NR$^{13}R^{14}$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, and —C($R^{14}$)=N(O$R^{14}$);

$R^{12A}$, when a substituent on carbon, is independently selected at each occurrence from the group consisting of;

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, —$CO_2H$, hydroxamic acid, hydrazide, boronic acid, sulfonamide, formyl, $C_3$–$C_6$ cycloalkoxy, —O$R^{13A}$, $C_1$–$C_4$ alkyl substituted with —$NH_2$, —$NH_2$, —NHMe, $C_2$–$C_6$ alkoxyalkyl optionally substituted with —Si($CH_3$)$_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$Me, —$SO_2NH_2$, —$NHSO_2Me$, —$OCH_2CO_2R^{13A}$, 2-(1-morpholino)ethoxy;

a 5- or 6-membered heterocyclic ring containing from 1 to 4 heteroatoms independently selected from oxygen, nitrogen or sulfur;

$R^{12A}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NH_2$; and when $R^{12A}$ is attached to a saturated carbon atom, it may be =O or =S; or when $R^{12A}$ is attached to sulfur it may be =O.

$R^{12A}$, when a substituent on nitrogen, is independently selected at each occurrence from the group consisting of;

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, and $C_1$–$C_4$ alkylcarbonyl;

$R^{13}$ is independently selected at each occurrence from the group consisting of;

H; heterocycle substituted with 0–3 $R^{11A}$ and 0–1 $R^{16}$; phenyl substituted with 0–3 $R^{11A}$; benzyl substituted with 0–3 $R^{11A}$; $C_1$–$C_6$ alkyl substituted with 0–3 $R^{11A}$; $C_2$–$C_4$ alkenyl substituted with 0–3 $R^{11A}$; $C_1$–$C_6$ alkylcarbonyl substituted with 0–3 $R^{11A}$; $C_1$–$C_6$ alkoxycarbonyl substituted with 0–3 $R^{11A}$; $C_1$–$C_6$ alkylaminocarbonyl substituted with 0–3 $R^{11A}$;

$C_3$–$C_6$ alkoxyalkyl substituted with 0–3 $R^{11A}$; an amine protecting group when $R^{13}$ is bonded to N; and a hydroxyl protecting group when $R^{13}$ is bonded to O;

$R^{14}$ is independently selected at each occurrence from the group consisting of;

hydrogen, $C_1$–$C_6$ alkoxy, $C_2$–$C_6$ alkenyl, phenyl, benzyl, an amine protecting group when $R^{14}$ is bonded to N, a hydroxyl or carboxyl protecting group when $R^{14}$ is bonded to O; and $C_1$–$C_6$ alkyl substituted with 0–3 groups selected from OH, $C_1$–$C_4$ alkoxy, halogen, $R^{13}$ and $R^{14}$ can alternatively join to form —($CH_2$)$_4$—, —($CH_2$)$_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group consisting of:

H and $C_1$–$C_6$ alkyl;

$R^{13A}$ and $R^{14A}$ can alternatively join to form —($CH_2$)$_4$—, —($CH_2$)$_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, —CN, —$NO_2$, $C_1$–$C_4$ haloalkyl, $C_1$–$C_4$ haloalkoxy, $C_1$–$C_4$ alkoxy, $C_1$–$C_6$ alkyl, $C_2$–$C_4$ alkenyl, $C_2$–$C_4$ alkynyl, phenethyl, phenoxy, $C_3$–$C_{10}$ cycloalkyl, $C_3$–$C_6$ cycloalkylmethyl, $C_7$–$C_{10}$ aralkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, CN, $NO_2$, $CF_3$, $C_1$–$C_4$ alkyl, $C_1$–$C_4$ alkoxy or OH; or $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

m is 0, 1 or 2;

$R^{22}$ and $R^{23}$ are independently selected at each occurrence from the group consisting of;

$C_1$–$C_8$ alkyl substituted with 0–3 $R^{31}$; $C_2$–$C_8$ alkenyl substituted with 0–3 $R^{31}$; $C_2$–$C_8$ alkynyl substituted with 0–3 $R^{31}$; a $C_3$–$C_{14}$ carbocyclic ring system substituted with 0–5 $R^{31}$ and 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is independently selected at each occurrence from the group consisting of;

—OH, $C_1$–$C_4$ alkoxy, —$CO_2R^{15}$, —$COR^{15}$, keto, halogen, cyano, —$CH_2NR^{13}R^{14}$, —$NR^{13}R^{14}$, —$CO_2R^{13}$, —C(=O)$R^{11}$, —OC(=O)$R^{13}$, —$OR^{13}$, $C_2$–$C_6$ alkoxyalkyl, —S(O)$_m R^{13}$, —NHC(=NH)NH$R^{13}$, —C(=NH)NH$R^{13}$, —C(=O)$NR^{13}R^{14}$, —$NR^{14}C(=O)R^{13}$, =NO$R^{14}$, —$NR^{14}C(=O)OR^{14}$, —OC(=O) $NR^{13}R^{14}$, —$NR^{13}C(=O)NR^{13}R^{14}$, —$NR^{13}C(=S)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_6$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —C($R^{14}$)=N(O$R^{14}$);

a $C_5$–$C_{14}$ carbocyclic residue substituted with 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is independently selected at each occurrence from the group consisting of;

phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, sulfonamide, —CHO, C$_3$–C$_6$ cycloalkoxy, —NR$^{13}$R$^{14}$, —C(R$^{14}$)=N(OR$^{14}$), —NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —B(OH)$_2$, —OCO$_2$R$^{13}$, phenyl, —C(=O)NR$^{13}$—(C$_1$–C$_4$ alkyl)—NR$^{13}$R$^{14}$, —C(=O)NR$^{40}$R$^{41}$, C$_1$–C$_4$ haloalkyl, C$_1$–C$_4$ haloalkoxy, C$_2$–C$_4$ haloalkenyl, C$_1$–C$_4$ haloalkynyl; —C(=O)NR$^{13}$C(R$^{11}$)$_2$NR$^{13}$R$^{14}$, —C(=O)NR$^{13}$C(R$^{11}$)$_2$ NR$^{13}$CO$_2$R$^{13}$, —C(=O)NR$^{13}$—(C$_1$–C$_4$ alkyl)—NR$^{13}$CO$_2$R$^{13}$, —C(=O)N(R$^{13}$)—(C$_1$–C$_4$ alkyl)—R$^{11}$, —C(=O)C(R$^{11}$)$_2$NR$^{13}$R$^{14}$, —C(=O)C(R$^{11}$)$_2$NR$^{13}$CO$_2$R$^{13}$, —C(=O)—(C$_1$–C$_4$ alkyl)—NR$^{13}$R$^{14}$, —C(=O)—(C$_1$–C$_4$ alkyl)—NR$^{13}$CO$_2$R$^{13}$; —(CH$_2$)$_p$OR$^{13}$, —(CH$_2$)$_p$NHR$^{13}$, —(CH$_2$)$_p$CONHR$^{13}$, —(CH$_2$)$_p$SO$_2$NHR$^{13}$, —(CH$_2$)$_n$NHCOR$^{13}$, —(CH$_2$)$_p$NHCO$_2$R$^{13}$, —(CH$_2$)$_n$OCONHR$^{13}$, —(CH$_2$)$_p$NHCONHR$^{13}$, —(CH$_2$)$_p$C(=NH)NHR$^{13}$;

C$_1$–C$_4$ alkoxy substituted with 0–4 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH;

C$_1$–C$_4$ alkyl substituted with 0–4 groups selected from: R$^{11}$, =NR$^{14}$, =NNR$^{13}$C(=O)NR$^{13}$R$^{14}$, =NNR$^{13}$C(=O)OR$^{13}$, or —NR$^{13}$R$^{14}$;

C$_2$–C$_4$ alkenyl substituted with 0–4 R$^{11}$, C$_2$–C$_4$ alkynyl substituted with 0–4 R$^{11}$;

a 5- or 6-membered heterocyclic ring containing from 1 to 4 heteroatoms independently selected from oxygen, nitrogen or sulfur, substituted with 0–2 R$^{12}$;

R$^{32}$ may be a 3- or 4- carbon chain attached to adjacent carbons on the ring to form a fused 5- or 6-membered ring, said 5- or 6- membered ring being optionally substituted on the aliphatic carbons with halogen, C$_1$–C$_4$ alkyl, C$_1$–C$_4$ alkoxy, hydroxy, or —NR$^{13}$R$^{14}$;

when R$^{32}$ is attached to a saturated carbon, it may be =O, =S, =NOH; and when R$^{32}$ is attached to sulfur it may be =O;

p is 0, 1, or 2 n is 1 or 2;

R$^{32}$, when a substituent on nitrogen, is independently selected at each occurrence from the group consisting of;

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, C$_1$–C$_4$ alkylcarbonyloxy, C$_1$–C$_4$ alkylcarbonyl, and —C (R$^{14}$)=N(OR$^{14}$);

R$^{40}$ is selected from: H or C$_1$–C$_3$ alkyl; and

R$^{41}$ is selected from:
—C(=O)NR$^{13}$R$^{14}$; C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$; —C(=O)H;
—C(=O)R$^{11}$; —C(=O)—(C$_1$–C$_4$ alkyl)—NR$^{13}$R$^{14}$; —C(=O)—(C$_1$–C$_4$ alkyl)—NR$^{13}$CO$_2$R$^{13}$; or 1–3 amino acids linked together via amide bonds, and linked to the N atom via the carboxylate terminus; and all functional groups, such as amines, carboxyls, ketones, aldehydes, hydrazines, guanidines, hydroxaminc acids, alcohols, oximes, and thiols, that are reactive with the chemistry of this process are protected in such a form that the protecting groups may be kept or removed;

said process comprising the steps of:

step (3c): contacting a compound of the formula (III)

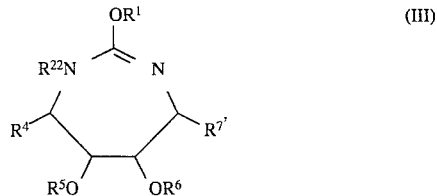

(III)

wherein:

R$^1$ is methyl or ethyl; and

R$^5$ and R$^6$ are the same and are selected from the group consisting of:

C$_1$–C$_6$ alkyl substituted with 0–3 R$^{11}$; C$_3$–C$_6$ alkoxyalkyl substituted with 0–3 R$^{11}$; C$_1$–C$_6$ alkylcarbonyl substituted with 0–3 R$^{11}$; C$_1$–C$_6$ alkoxycarbonyl substituted with 0–3 R$^{11}$; C$_1$–C$_6$ alkylaminocarbonyl substituted with 0–3 R$^{11}$; benzoyl substituted with 0–3 R$^{12}$; phenoxycarbonyl substituted with 0–3 R$^{12}$; phenylaminocarbonyl substituted with 0–3 R$^{12}$; a hydroxyl protecting; and any group that, when administered to a mammalian subject, cleaves to form a free hydroxyl group; or R$^5$ and R$^6$ may alternatively be taken together, along with the oxygen atoms to which they are attached, to form a group selected from the group consisting of:
—O—C(—CH$_2$CH$_2$CH$_2$CH$_2$CH$_2$—)—O—,
—O—C(CH$_2$CH$_3$)$_2$—O—, —O—C(CH$_3$)(CH$_2$CH$_3$)—O—, —O—C(CH$_2$CH$_2$CH$_2$CH$_3$)$_2$—O—, —O—C(CH$_3$)(CH$_2$CH(CH$_3$)CH$_3$)—O—,
—O—CH(phenyl)—O—, —OCH$_2$SCH$_2$O—,
—OCH$_2$OCH$_2$O—, —OS(=O)O—,
—OC(=O)O—, —OCH$_2$O—, —OC(=S)O—,
—OS(=O)$_2$O—, —OC(=O)C(=O)O—,
—OC(CH$_3$)$_2$O—, and —OC(OCH$_3$)(CH$_2$CH$_2$CH$_3$)O—; and all other substituents are as defined above;

in a solvent with at least 2 molar equivalents of an isourea oxygen dealkylating agent for a period of time sufficient to form a compound of the formula (V)

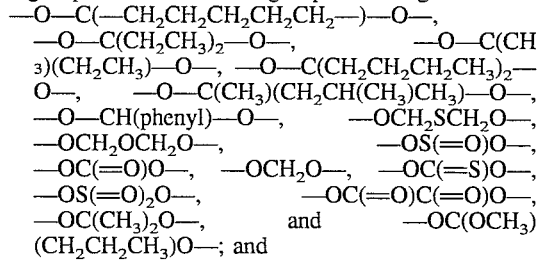

(V)

which is optionally isolated; and step (4d): contacting a compound of the formula (V) with a reagent or condition or combination of reagents and or conditions for a period of time sufficient to effect the removal of R$^5$ and R$^6$ and to form a compound of the formula (VIa).

4. The method of claim 3 wherein a compound of the formula (VIa) is made by:

step (3b): contacting a compound of the formula (III) with a reagent or condition or combination of reagents and/or conditions for a period of time sufficient to effect the removal of R$^5$, R$^6$ and R$^1$ and to form a compound of the formula (VIa).

5. The method of claim 1, claim 2, claim 3 or claim 4 wherein a compound of the formula (III) is made by:

step (2): contacting a compound of the formula (II)

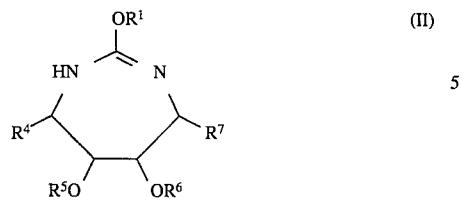

in an aprotic solvent with at least one molar equivalent of a strong base and at least one molar equivalent of a nitrogen alkylating agent $R^{22}$-Z (where $R^{22}$ is as defined for compounds of the formula (VIa) and (VIb) and Z is leaving group such as halide or sulfonate) for a period of time sufficient to form a compound of the formula (III).

6. The method of claim 5 wherein a compound of the formula (II) is made by:

step (1a): contacting a compound of the formula (X)

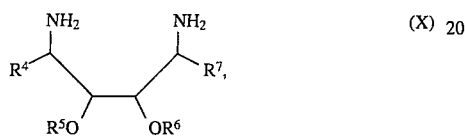

in a solvent with an excess of a tetralkylorthocarbonate, $(R^1-O)_4C$, wherein $R^1$ is methyl or ethyl, in the presence of an acid at a suitable temperature for a period of time sufficient to form a compound of the formula (II).

7. The method of claim 5 wherein a compound of the formula (II) is made by:

step (1b): contacting, at an appropriate rate, a compound of the formula (X), optionally in the presence of a hindered amine base, in an aprotic solvent with at least 1 molar equivalent of a cyclizing agent at a temperature of ambient to solvent reflux for a period of time sufficient to form a compound of the formula (I)

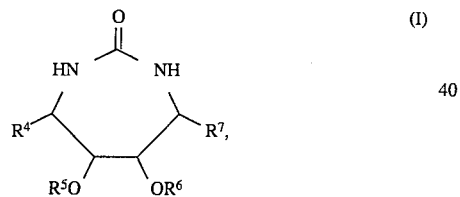

wherein all substituents are as defined above, which is optionally isolated; and contacting a compound of the formula (I) in an aprotic solvent with 1–2 molar equivalents of an oxygen alkylating agent ($R^1$-Y), wherein $R^1$ is as defined above and Y is $'OSO_2CF_3$, $—OSO_2$-aryl, $—CH_3CH_2)_2OBF_4$, or $—(CH_3)_2OBF_4$, for a period of time sufficient to form a compound of the formula (II).

8. The method of claim 1 or claim 3 wherein:

$R^4$ and $R^7$ are independently selected at each occurrence from the group consisting of:
  $C_1$–$C_8$ alkyl substituted with 0–3 $R^{11}$; and
  $C_2$–$C_8$ alkenyl substituted with 0–3 $R^{11}$;

$R^{11}$ is independently selected at each occurrence from the group consisting of:
  H, keto, halogen, cyano, $—CH_2NR^{13}R^{14}$, $—NR^{13}R^{14}$, $—CO_2R^{13}$, $—OC(=O)R^{13}$, $—OR^{13}$, $—S(O)_mR^{13}$, $C_2$–$C_4$ alkenyl, $C_3$–$C_6$ cycloalkylmethyl, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl), substituted with 0–2 $R^{12}$, a $C_5$–$C_{14}$ carbocyclic residue substituted with 0–3 $R^{12}$; and
  a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is independently selected at each occurrence from the group consisting of:
  H, keto, halogen, cyano, $—CH_2N(R^{13A})R^{(14A)}$, $—OR^{13A}$, $—N(R^{13A})R^{(14A)}$, $C_2$–$C_4$ alkenyl, $C_3$–$C_6$ cycloalkylmethyl, $C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;
  $NO_2$, $C_1$–$C_6$ alkyl, or phenyl, said phenyl being optionally substituted with Cl, F, Br, CN, $NO_2$, $CF_3$, $OCH_3$ or OH; and
  a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is independently selected at each occurrence from the group consisting of:
  phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, $—OR^{13}$, $C_2$–$C_6$ alkoxyalkyl optionally substituted with $—Si(CH_3)_3$, $C_1$–$C_4$ hydroxyalkyl, methylenedioxy, ethylenedioxy, $—S(O)_mR^{13}$, $CF_3$, 2-(1-morpholino)ethoxy, $—CO_2H$, hydroxamic acid, hydrazide, $—C(R^{14})=N(OR^{14})$, sulfonamide; and
  a 5- or 6-membered heterocyclic ring containing from 1 to 4 heteroatoms independently selected from oxygen, nitrogen or sulfur.

$R^{12}$, when a substituent on nitrogen, is independently selected at each occurrence from the group consisting of:
  benzyl and methyl;

$R^{12A}$, when a substituent on carbon, is independently selected at each occurrence from the group consisting of:
  phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, $—OR^{13A}$, $C_2$–$C_6$ alkoxyalkyl optionally substituted with $—Si(CH_3)_3$, $—S(O)_mMe$; and
  a 5- or 6-membered heterocyclic ring containing from 1 to 4 heteroatoms independently selected from oxygen, nitrogen or sulfur.

$R^{12A}$, when a substituent on nitrogen, is independently selected at each occurrence from the group consisting of:
  phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkoxycarbonyl, $C_1$–$C_4$ alkylcarbonyloxy, $C_1$–$C_4$ alkylcarbonyl, $CF_3$, 2-(1-morpholino)ethoxy, $—CO_2H$, hydroxamic acid, hydrazide, $—C(R^{14A})=N(OR^{14A})$, and sulfonamide;

$R^{13}$ is independently selected at each occurrence from the group consisting of:
  a heterocycle selected from the group consisting of:

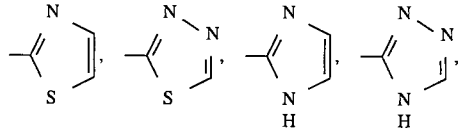

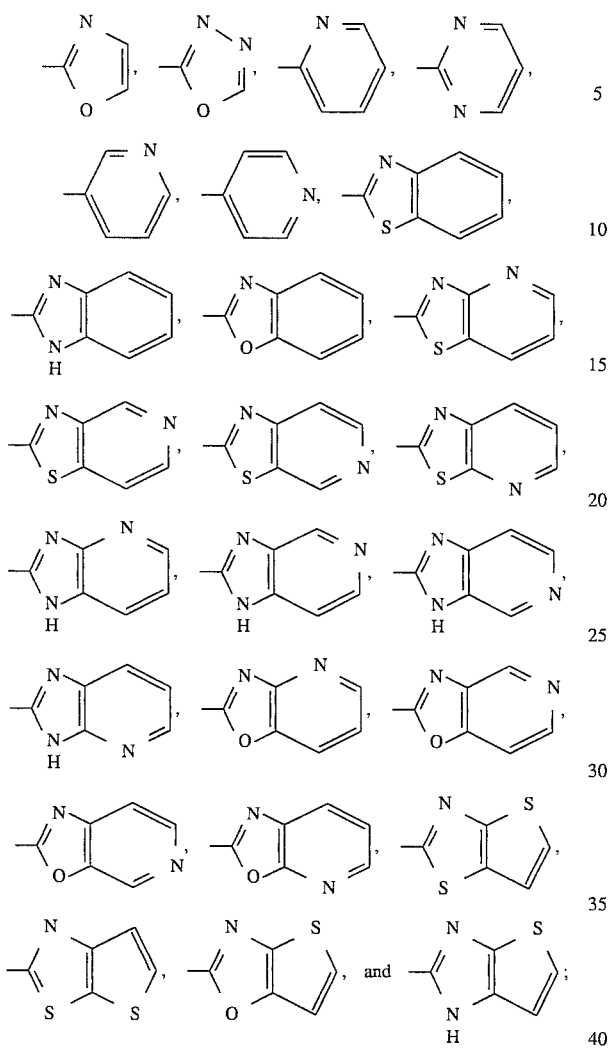

said heterocycle substituted with 0–3 $R^{11A}$ and 0–1 $R^{16}$;
H; $C_1$–$C_6$ alkyl substituted with 0–3 $R^{11A}$; $C_3$–$C_6$ alkoxyalkyl substituted with 0–3 $R^{11A}$; $C_2$–$C_4$ alkenyl substituted with 0–3 $R^{11A}$; benzyl substituted with 0–3 $R^{11A}$; an amine protecting group when $R^{13}$ is bonded to N; and a hydroxyl or carboxyl protecting group when $R^{13}$ is bonded to O;

$R^{14}$ is independently selected at each occurrence from the group consisting of:
hydrogen, $CF_3$, $C_1$–$C_6$ alkyl, $C_1$–$C_6$ alkoxy, $C_2$–$C_6$ alkenyl, benzyl, an amine protecting group when $R^{14}$ is bonded to N, and a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected at each occurrence from the group consisting of:
H and $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected at each occurrence from the group consisting of:
halogen, $NO_2$, CN, $C_1$–$C_6$ alkyl, and phenyl, said phenyl being optionally substituted with Cl, F, Br, CN, $NO_2$, $CF_3$, $OCH_3$ or OH;

$R^{22}$ and $R^{23}$ are independently selected at each occurrence from the group consisting of:
$C_1$–$C_8$ alkyl substituted with 0–3 $R^{31}$; $C_2$–$C_8$ alkenyl substituted with 0–3 $R^{31}$; $C_2$–$C_4$ alkynyl substituted with 0–3 $R^{31}$; a $C_6$–$C_{10}$ aryl substituted with 0–3 $R^{31}$ and 0–3 $R^{32}$; and a heterocycle selected from the group consisting of thiazole, indazole, thieno[2,3-c]pyrazole and thieno[3,2-c]pyrazole, said heterocycle substituted with 0–2 $R^{31}$;

$R^{31}$ is independently selected at each occurrence from the group consisting of:
—OH, $C_1$–$C_4$ alkoxy, cyano, nitro, $C_1$–$C_4$ haloalkyl, $C_1$–$C_4$ haloalkoxy, —$CO_2R^{15}$, —$COR^{15}$, keto, halogen, —$CH_2NR^{13}R^{14}$, —$NR^{13}R^{14}$, —$OR^{13}$, $C_2$–$C_6$ alkoxyalkyl, $C_1$–$C_4$ alkyl, $C_2$–$C_4$ alkenyl, $C_3$–$C_{10}$ cycloalkyl, —$CO_2R^{13}$, —$S(O)_mR^{13}$;
a $C_5$–$C_{14}$ carbocyclic residue substituted with 0–5 $R^{32}$; and a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is independently selected at each occurrence from the group consisting of:
phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, —$CONR^{13}NR^{13}R^{14}$, cyano, sulfonamide, —CHO, $C_3$–$C_6$ cycloalkoxy, —$NR^{13}R^{14}$, —$NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)— $NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl; —$(CH_2)_pOR^{13}$, —$(CH_2)_pNHR^{13}$, —$(CH_2)_pCONHR^{13}$, —$(CH_2)_pSO_2NHR^{13}$, —$(CH_2)_nOCONHR^{13}$, —$(CH_2)_pNHCONHR^{13}$, —$(CH_2)_pC(=NH)NHR^{13}$; $C(=O)C(R^{11})_2NR^{13}R^{14}$;
—$C(=O)C(R^{11})_2NR^{13}CO_2R^{13}$;
—$C(=O)C(R^{11})_2NR^{13}CO_2R^{13}$; —$C(=O)$—($C_1$–$C_4$ alkyl)— $NR^{13}R^{14}$; —$C(=O)$—($C_1$–$C_4$ alkyl)—$NR^{13}CO_2R^{13}$;

$C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, or —$NR^{13}R^{14}$;

$C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$;

$C_2$–$C_4$ alkenyl substituted with 0–4 $R^{11}$, $C_2$–$C_4$ alkynyl substituted with 0–3 $R^{11}$; and a 5- or 6-membered heterocyclic ring containing from 1 to 4 heteroatoms independently selected from oxygen, nitrogen or sulfur, substituted with 0–2 $R^{12}$; and $R^{32}$, when a substituent on nitrogen, is independently selected at each occurrence from the group consisting of:
phenyl, benzyl, phenethyl, hydroxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$-$C_6$ alkoxyalkyl, $C_1$-$C_4$ alkoxycarbonyl, $C_1$-$C_4$ alkylcarbonyloxy, and $C_1$-$C_4$ alkylcarbonyl.

9. The method of claim 8 wherein:

$R^4$ and $R^7$ are independently selected from:
  $C_1$-$C_8$ alkyl substituted with 0–2 $R^{11}$;

$R^{11}$ is independently selected at each occurrence from the group consisting of:
  H, halogen, —$OR^{13}$, $C_3$-$C_{10}$ cycloalkyl substituted with 0–2 $R^{12}$, $C_1$-$C_4$ alkyl substituted with 0–2 $R^{12}$, aryl($C_1$-$C_3$ alkyl)- substituted with 0–2 $R^{12}$; aryl substituted with 0–2 $R^{12}$; and
  a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{11A}$ is independently selected at each occurrence from the group consisting of:
  H, halogen, —$OR^{13A}$, $C_3$-$C_{10}$ cycloalkyl substituted with 0–2 $R^{12A}$, $C_1$-$C_4$ alkyl substitued with 0–2 $R^{12A}$, aryl($C_1$-$C_3$ alkyl)- substituted with 0–2 $R^{12A}$, aryl substituted with 0–2 $R^{12A}$;
  $NO_2$, cyano, $C_1$-$C_6$ alkyl, or phenyl, said phenyl being optionally substituted with Cl, F, Br, CN, $NO_2$, $CF_3$, $OCH_3$ or OH; and
  a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is independently selected at each occurrence from the group consisting of:
  benzyloxy, halogen, methyl, nitro, cyano, $C_3$-$C_6$ cycloalkyl, $C_3$-$C_6$ cycloalkylmethyl, $C_7$-$C_{10}$ arylalkyl, $C_1$-$C_4$ alkoxy, formyl, $C_3$-$C_6$ cycloalkoxy, —$OR^{13}$, $C_2$-$C_6$ alkoxyalkyl optionally substituted with —$Si(CH_3)_3$, —$S(O)_m$Me, $CF_3$, 2-(1-morpholino)ethoxy, hydroxamic acid, hydrazide, —$C(R^{14})$=$N(OR^{14})$, and sulfonamide;

$R^{12}$, when a substituent on nitrogen, is methyl;

$R^{12A}$, when a substituent on carbon, is independently selected at each occurrence from the group consisting of:
  benzyloxy, halogen, methyl, nitro, cyano, $C_3$-$C_6$ cycloalkyl, $C_3$-$C_6$ cycloalkylmethyl, $C_7$-$C_{10}$ arylalkyl, $C_1$-$C_4$ alkoxy, formyl, $C_3$-$C_6$ cycloalkoxy, —$OR^{13A}$, $C_2$-$C_6$ alkoxyalkyl optionally substituted with —$Si(CH_3)_3$, —$S(O)_m$Me, $CF_3$, 2-(1-morpholino)ethoxy, —$CO_2H$, hydroxamic acid, hydrazide, —$C(R^{14A})$=$N(OR^{14A})$, and sulfonamide;

$R^{12A}$, when a substituent on nitrogen, is independently selected at each occurrence from the group consisting of:
  benzyl and methyl;

$R^{13}$ is independently selected at each occurrence from the group consisting of:
  a heterocycle selected from the group consisting of:

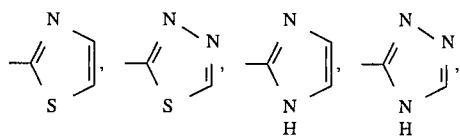

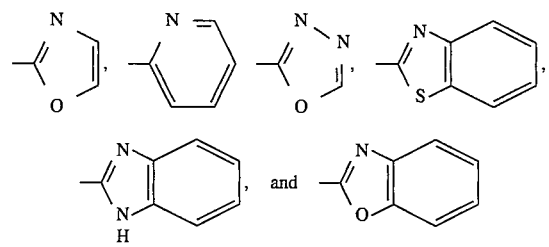

said heterocycle substituted with 0–1 $R^{11A}$ and 0–1 $R^{16}$;
H, $C_1$-$C_4$ alkyl, $C_2$-$C_4$ alkenyl, benzyl, an amine protecting group when $R^{13}$ is bonded to N, and a hydroxyl or carboxyl protecting group when $R^{13}$ is bonded to O;

$R^{14}$ is independently selected from the group consisting of:
  hydrogen, $CF_3$, $C_1$-$C_4$ alkyl, $C_1$-$C_4$ alkoxy, $C_2$-$C_4$ alkenyl, benzyl, an amine protecting group when $R^{14}$ is bonded to N, and a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$-$C_6$ or alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{22}$ and $R^{23}$ are independently selected at each occurrence from the group consisting of:
  $C_1$-$C_8$ alkyl substituted with 0–2 $R^{31}$; $C_2$-$C_6$ alkenyl substituted with 0–2 $R^{31}$; phenyl substituted with 0–2 $R^{31}$ and 0–2 $R^{32}$; and
  a heterocycle selected from the group consisting of thiazole, indazole, thieno[2,3-c]pyrazole and thieno [3,2-c]pyrazole, said heterocycles substituted with 0–2 $R^{31}$;

$R^{31}$ is independently selected from the group consisting of:
  —OH, —$OCH_3$, cyano, nitro, $CF_3$, $C_1$-$C_4$ haloalkoxy, —$CO_2R^{15}$, —$COR^{15}$, halogen, —$OR^{13}$, $C_1$-$C_4$ alkyl, $C_3$-$C_{10}$ cycloalkyl, —$CO_2R^{13}$, —$S(O)_mR^{13}$; aryl substituted with 0–3 $R^{32}$; and
  a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is independently selected at each occurrence from the group consisting of:
  —$(CH_2)_pOR^{13}$, —$(CH_2)_pCONHR^{13}$, —$(CH_2)_nOCONHR^{13}$, —$(CH_2)_pNHCONHR^{13}$; —$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})$=$N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —$OCONHCH_2C_6H_5$, —$OCONHCH_3$, oxazolidinyl, —C≡C=$CH_2OH$, —COCH₃, hydroxyethyl, C₁–C₃ alkyl (said alkyl substituted with 0–4 halogen, or OH), tetrazolyl, —OCH₂CONH₂, —CONHNH₂, —CH=NNHCONH₂, —CONHOCH₃, —CH₂CH(OH)CH₂OH, adamantamido, hydroxyethoxy, dihydroxyethyl, —C(NH₂)=NH, —CONHCH₃, —B(OH)₂, benzyloxy, —CONHCH₂CH₃, —CON(CH₂CH₃)₂, methylthio, —SO₂CH₃, —NHCONH₂, —NHCONHCH₃, —NHCOCH₂N(CH₃)₂, NHCOCH₂NHCH₃, —NHCOCH₂NHCO₂CH₂C₆H₅, —NHCOCH₂NH₂, —NHCOCH(CH₃)NHCO₂CH₂C₆H₅, —NHCOCH(CH₂C₆H₅)NHCO₂CH₂C₆H₅, —NHCOCH(CH₃)NH₂, —NHCOCH(CH₂C₆H₅)NH₂, —CO₂CH₂CH₃, —CONHCH₂CH₂CH₃, —CONHCH(CH₃)₂, —CH₂-imidazole, —COC(CH₃)₃, —CH(OH)CF₃, —CO-imidazole, —CO— pyrazolyl, oxadiazolidinonyl, —COCF₃, —COCH₂CH₃, —COCH₂CH₂CH₃, pyrazolyl, —SO₂NH₂, —C(CH₂CH₃)=N(OH), —C(CF₃)=N(OH), phenyl, acetoxy, hydroxyamino, —N(CH₃)(CHO), cyclopropylmethoxy, —CONR¹³R¹⁴, —CONHOH, (diethylaminoethyl)aminocarbonyl, (N-ethyl, N-methylaminoethyl)aminocarbonyl, (4-methylpiperazinylethyl)aminocarbonyl, (pyrrolidinylethyl)aminocarbonyl, (piperidinylethyl)aminocarbonyl, —NHCOCH₂NHCH₃, N-(2-(4-morpholino)ethyl)aminocarbonyl, and N-(2-(N,N-dimethylamino)ethyl)aminocarbonyl;

p is 0; and $R^{32}$, when a substituent on nitrogen, is independently selected at each occurrence from the group consisting of:
benzyl and methyl.

10. The method of claim 9 wherein:

$R^4$ and $R^7$ are independently $C_1$–$C_3$ alkyl substituted with 0–1 $R^{11}$;

$R^{12A}$, when a substituent on nitrogen, is methyl;

$R^{13}$ is independently selected from the group consisting of:
a heterocycle selected from the group consisting of:

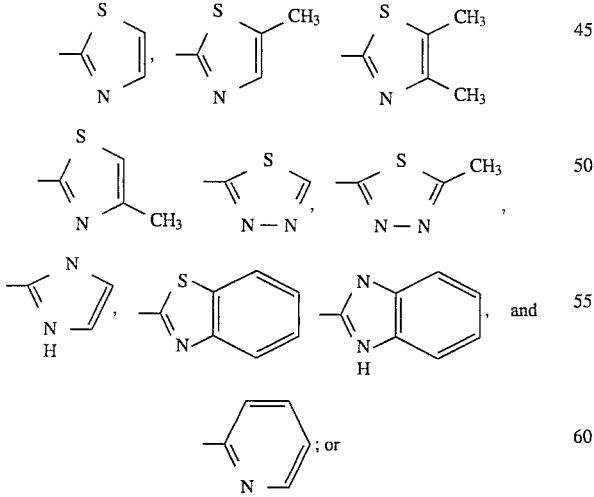

H, C₁–C₄ alkyl, C₂–C₄ alkenyl, benzyl, an amine protecting group when R¹³ is bonded to N, and a hydroxyl or carboxyl protecting group when R¹³ is bonded to O;

R¹³ and R¹⁴ can alternatively join to form —(CH₂)₄—, —(CH₂)₅—, —CH₂CH₂N(R¹⁵)CH₂CH₂—, or —CH₂CH₂OCH₂CH₂—;

$R^{13A}$ and $R^{14A}$ are independently selected from: H or C₁–C₆ alkyl;

$R^{13A}$ and $R^{14A}$ can alternatively join to form —(CH₂)₄—, —(CH₂)₅—, —CH₂CH₂N(R¹⁵)CH₂CH₂—, or —CH₂CH₂OCH₂CH₂—;

$R^{15}$ is H or CH₃;

$R^{22}$ and $R^{23}$ are independently selected from the group consisting of:
C₁–C₈ alkyl substituted with 0–2 R³¹; benzyl substituted with 0–2 R³¹ and 0–2 R³²; and
a heterocycle selected from the group consisting of thiazole, indazole, thieno[2,3-c]pyrazole and thieno[3,2-c]pyrazole, said heterocycle substituted with 0–2 R³¹;

$R^{32}$, when a substituent on carbon, is independently selected from the group consisting of:
—(CH₂)ₚOR¹³, —(CH₂)ₚCONHR¹³, —CONH₂, —CO₂H, —CHO, —CH₂NHOH, —CH₂NR¹³R¹⁴, —NR¹³R¹⁴, hydroxy, hydroxymethyl, —C(R¹⁴)=N(OR¹⁴), halogen, methoxy, methyl, nitro, cyano, allyloxy, —CO₂CH₃, —NHCHO, —NHCOCH₃, —OCO₂CH₃, —CH=NCH₂CH₂OH, —OCONHCH₂C₆H₅, —OCONHCH₃, oxazolidinyl, —C≡C—CH₂OH, —COCH₃, hydroxyethyl, C₁–C₃ alkyl (said alkyl substituted with 0–4 halogen, or OH), tetrazolyl, —OCH₂CONH₂, —CONHNH₂, —CH=NNHCONH₂, —CONHOCH₃, —CH₂CH(OH)CH₂OH, adamantamido, hydroxyethoxy, dihydroxyethyl, —C(NH₂)=NH, —CONHCH₃, —B(OH)₂, benzyloxy, —CONHCH₂CH₃, —CON(CH₂CH₃)₂, methylthio, —SO₂CH₃, —NHCONH₂, —NHCONHCH₃, —NHCOCH₂N(CH₃)₂, —NHCOCH₂NHCH₃, —NHCOCH₂NHCO₂CH₂C₆H₅, —NHCOCH₂NH₂, —NHCOCH(CH₃)NHCO₂CH₂C₆H₅, —NHCOCH(CH₂C₆H₅)NHCO₂CH₂C₆H₅, —NHCOCH(CH₃)NH₂, —NHCOCH(CH₂C₆H₅)NH₂, —CO₂CH₂CH₃, —CONHCH₂CH₂CH₃, —CONHCH(CH₃)₂, —CH₂-imidazole, —COC(CH₃)₃, —CH(OH)CF₃, —CO—imidazole, —CO—pyrazolyl, oxadiazolidinonyl, —COCF₃, —COCH₂CH₃, —COCH₂CH₂CH₃, pyrazolyl, —SO₂NH₂, —C(CH₂CH₃)=N(OH), —C(CF₃)=N(OH), phenyl, acetoxy, hydroxyamino, —N(CH₃)(CHO), cyclopropylmethoxy, —CONR¹³R¹⁴, —CONHOH, (diethylaminoethyl)aminocarbonyl, (N-ethyl, N-methylaminoethyl)aminocarbonyl, (4-methylpiperazinylethyl)aminocarbonyl, (pyrrolidinylethyl)aminocarbonyl, (piperidinylethyl)aminocarbonyl, —NHCOCH₂NHCH₃, N—(2-(4-morpholino)ethyl)aminocarbonyl, and N-(2 -(N,N-dimethylamino)ethyl)aminocarbonyl;

p is 0; and

R³², when a substituent on nitrogen, is methyl.

11. The method of claim 10 wherein:

R⁴ and R⁷ are independently selected from the group consisting of:
benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl, thiomethylbenzyl, thiazolylmethyl, 3,4-methylenedioxybenzyl, and N,N-dimethylaminobenzyl;

$R^{22}$ and $R^{23}$ are independently selected from the group consisting of:

allyl, methyl, ethyl, propyl, cyclopropyl, cyclopropylmethyl, cyclobutylmethyl, n-butyl, i-butyl, $CH_2CH=C(CH_3)_2$, pyridylmethyl, pyridyl, methallyl, n-pentyl, i-pentyl, hexyl, phenyl, benzyl, isoprenyl, propargylmethyl, picolinylmethyl, methoxymethyl, cyclohexylmethyl, dimethylbutyl, ethoxymethyl, napthylmethyl, methyloxazolinylmethyl, naphthyl, methyloxazolinyl, vinyloxymethyl, pentafluorobenzyl, quinolinylmethyl, carboxybenzyl, chlorothienylmethyl, benzyloxybenzyl, biphenylmethyl, phenylbenzyl, adamantylmethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutyl, formaldoximebenzyl, cyclopentyl, cyclopentylmethyl, nitrobenzyl, $(H_2NC(=O))$-benzyl, carbomethoxybenzyl, carboethoxybenzyl, tetrazolylbenzyl, dimethylallyl, aminomethylbenzyl, (O-benzyloformaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl (oxazolidinyl)-benzyl, (hydroxy)pentyl, pentenyl, (hydroxy)heptyl, (hydroxy)butyl, (carboxy)butyl, (carbomethoxy)butyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N,-N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, $(H_2NSO_2)$-benzyl, dihydroxyethylbenzyl, (MeHNC(=O)NH)-benzyl, $(H_2NC(=O)NH)$-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, $(CH_3NHC(=O)O)$-benzyl, $(NH_2C(=O)CH_2O)$benzyl, $(NH_2C(=NH))$benzyl, ((N-phenylmethoxycarbonyl)glycylamino)benzyl, (imidazolylmethyl)benzyl, $((CH_3)_3C—C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl, $(H_2NC(=NOH))$benzyl, $(H_2NC(=NOH))$fluorobenzyl, benzimidazolylmethyl, benzotriazolylmethyl, indazolylmethyl, benzoxazolinylmethyl, benzisoxazolylmethyl, thienylmethyl, furylmethyl, N-butylaminobenzyl, N,N-dimethylaminobenzyl, N-propylaminobenzyl, N-methylaminomethylbenzyl, carbomethoxybenzyl, N-methylaminocarbonylbenzyl,glycylaminobenzyl, N,N-dimethylaminocarbonylbenzyl, N,N-diethylaminobenzyl, alanylaminobenzyl, phenylalanylaminobenzyl, (N-methylglycyl)aminobenzyl, $(H_2NC(=NOH))$benzyl, $(CH_3C(=NOH))$benzyl, 2-amino-5-benzoxazolylmethyl, 3-amino-5-benzisoxazolylmethyl, 3-amino-5-indazolylmethyl, 3-methylamino-5-indazolylmethyl, 3-ethylamino-5-indazolylmethyl, 3-methyl-5-indazolylmethyl, 3-ethyl-5-indazolylmethyl, 3-methoxy-5-indazolylmethyl, 3-methoxycarbonyl-5-indazolylmethyl, 3-chloro-5-indazolylmethyl, 3,4-methylenedioxybenzyl, pyridylmethyl, 3-(2-thiazolylaminocarbonyl)benzyl, 3-(4-methyl-2-thiazolylaminocarbonyl)benzyl, 3-(1,3,4-thiadiazol-2-ylaminocarbonyl)benzyl, 3-(5-methyl-1,3,4-thiadiazol-2-ylaminocarbonyl)benzyl, 3-(5-t-butyl-1,3,4-thiadiazol-2-ylaminocarbonyl)benzyl, 3-(5-methyl-2-thiazolylaminocarbonyl)benzyl, 3-(4,5-dimethyl-2-thiazolylaminocarbonyl)benzyl, 3-(2-imidazolylaminocarbonyl)benzyl, 3-(2-pyridylaminocarbonyl)benzyl, 3-(2-benzothiazolylaminocarbonyl)benzyl, 3-(2-benzimidazolylaminocarbonyl)benzyl, 3-(2-thiazolyloxy)benzyl, and 3-(2-pyridinyloxy)benzyl.

* * * * *